United States Patent
Gu et al.

(10) Patent No.: US 11,896,800 B2
(45) Date of Patent: Feb. 13, 2024

(54) ENHANCED CANCER IMMUNOTHERAPY BY MICRONEEDLE PATCH-ASSISTED DELIVERY

(71) Applicant: NORTH CAROLINA STATE UNIVERSITY, Raleigh, NC (US)

(72) Inventors: Zhen Gu, Raleigh, NC (US); Chao Wang, Raleigh, NC (US); Yanqi Ye, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 783 days.

(21) Appl. No.: 16/081,188

(22) PCT Filed: Mar. 1, 2017

(86) PCT No.: PCT/US2017/020135
§ 371 (c)(1),
(2) Date: Aug. 30, 2018

(87) PCT Pub. No.: WO2017/151727
PCT Pub. Date: Sep. 8, 2017

(65) Prior Publication Data
US 2019/0083703 A1    Mar. 21, 2019

Related U.S. Application Data

(60) Provisional application No. 62/301,789, filed on Mar. 1, 2016.

(51) Int. Cl.
*A61K 9/00* (2006.01)
*A61M 5/158* (2006.01)
(Continued)

(52) U.S. Cl.
CPC .............. *A61M 5/158* (2013.01); *A61B 5/055* (2013.01); *A61B 5/1486* (2013.01);
(Continued)

(58) Field of Classification Search
CPC ...................................................... A61M 5/158
See application file for complete search history.

(56) References Cited

U.S. PATENT DOCUMENTS

| 8,217,149 B2 | 7/2012 | Irving et al. | |
| 2011/0195124 A1* | 8/2011 | Jin | A61K 9/0021 424/486 |

(Continued)

FOREIGN PATENT DOCUMENTS

| JP | 2012-504160 A | 2/2012 |
| JP | 2015-129114 A | 7/2015 |

(Continued)

OTHER PUBLICATIONS

Wolchok, Nivolumab plus Ipilimumab in Advanced Melanoma, The New England Journal of Medicine, 369(2), 2013, 122-133 (Year: 2013).*

(Continued)

*Primary Examiner* — Paul W Dickinson
(74) *Attorney, Agent, or Firm* — Meunier Carlin & Curfman LLC

(57) ABSTRACT

Disclosed herein are self-degradable microneedle devices for the controlled-release of an immunotherapeutic agent. Also disclosed are methods for treating a disease (for example, cancer) using a self-degradable microneedle patch for the sustained delivery of an immunotherapeutic agent (for example, a PD1 antibody).

10 Claims, 22 Drawing Sheets

(51) Int. Cl.

| | |
|---|---|
| A61B 5/1486 | (2006.01) |
| A61B 5/055 | (2006.01) |
| A61B 5/15 | (2006.01) |
| A61B 5/00 | (2006.01) |
| A61P 35/00 | (2006.01) |
| A61K 31/728 | (2006.01) |
| A61K 31/734 | (2006.01) |
| A61M 5/168 | (2006.01) |
| C07K 16/28 | (2006.01) |
| A61M 37/00 | (2006.01) |

(52) U.S. Cl.
CPC .. *A61B 5/150022* (2013.01); *A61B 5/150984* (2013.01); *A61B 5/41* (2013.01); *A61K 9/0021* (2013.01); *A61K 31/728* (2013.01); *A61K 31/734* (2013.01); *A61M 5/168* (2013.01); *A61P 35/00* (2018.01); *C07K 16/2803* (2013.01); *C07K 16/2896* (2013.01); *A61B 5/150969* (2013.01); *A61M 2037/0046* (2013.01); *A61M 2037/0061* (2013.01)

(56) References Cited

U.S. PATENT DOCUMENTS

| | | | |
|---|---|---|---|
| 2014/0336487 | A1 | 11/2014 | Wang |
| 2018/0291074 | A1* | 10/2018 | Chan ........................ A61P 35/02 |

FOREIGN PATENT DOCUMENTS

| | | |
|---|---|---|
| WO | 2011066389 | 6/2011 |
| WO | 2014012059 | 7/2014 |
| WO | 2014113679 A1 | 7/2014 |
| WO | 2015066535 A1 | 5/2015 |
| WO | 2016014530 A1 | 1/2016 |
| WO | 20160336487 | 1/2016 |

OTHER PUBLICATIONS

Bachelder, Eric M., et al. "Acetal-derivatized dextran: an acid-responsive biodegradable material for therapeutic applications." Journal of the American Chemical Society 130.32 (2008): 10494-10495.
Bryant, Stephanie J., Charles R. Nuttelman, and Kristi S. Anseth. "Cytocompatibility of UV and visible light photoinitiating systems on cultured NIH/3T3 fibroblasts in vitro." Journal of Biomaterials Science, Polymer Edition 11.5 (2000): 439-457.
Chapman, Andrew P. "PEGylated antibodies and antibody fragments for improved therapy: a review." Advanced drug delivery reviews 54.4 (2002): 531-545.
Chen, Jingyi, et al. "Immuno gold nanocages with tailored optical properties for targeted photothermal destruction of cancer cells." Nano letters 7.5 (2007): 1318-1322.
Chen, Qian, et al. "Nanoscale theranostics for physical stimulus-responsive cancer therapies." Biomaterials 73 (2015): 214-230.
Chiappini, Ciro, et al. "Biodegradable nanoneedles for localized delivery of nanoparticles in vivo: exploring the biointerface." ACS nano 9.5 (2015): 5500-5509.
Chinai, Jordan M., et al. "New immunotherapies targeting the PD-1 pathway." Trends in pharmacological sciences 36.9 (2015): 587-595.
Chinembiri, Tawona N., et al. "Review of natural compounds for potential skin cancer treatment." Molecules 19.8 (2014): 11679-11721.
Curran, Michael A., et al. "PD-1 and CTLA-4 combination blockade expands infiltrating T cells and reduces regulatory T and myeloid cells within B16 melanoma tumors." Proceedings of the National Academy of Sciences 107.9 (2010): 4275-4280.
DeMuth, Peter C., et al. "Polymer multilayer tattooing for enhanced DNA vaccination." Nature materials 12.4 (2013): 367-376.
Gittard, Shaun D., et al. "The effects of geometry on skin penetration and failure of polymer microneedles." Journal of adhesion science and technology 27.3 (2013): 227-243.
Gu, Zhen, et al. "Injectable nano-network for glucose-mediated insulin delivery." ACS nano 7.5 (2013): 4194-4201.
Gubin, Matthew M., et al. "Checkpoint blockade cancer immunotherapy targets tumour-specific mutant antigens." Nature 515.7528 (2014): 577-581.
Harvey, Alfred J., et al. "Microneedle-based intradermal delivery enables rapid lymphatic uptake and distribution of protein drugs." Pharmaceutical research 28.1 (2011): 107-116.
Irvine, Darrell J., et al. "Synthetic nanoparticles for vaccines and immunotherapy." Chemical reviews 115.19 (2015): 11109-11146.
Kyi, Chrisann, and Michael A. Postow. "Checkpoint blocking antibodies in cancer immunotherapy." FEBS letters 588.2 (2014): 368-376.
Larkin, James, et al. "Combined nivolumab and ipilimumab or monotherapy in untreated melanoma." New England journal of medicine 373.1 (2015): 23-34.
Lee, Dong-Keun, et al. "Nanodiamond-gutta percha composite biomaterials for root canal therapy." ACS nano 9.11 (2015): 11490-11501.
Lu, Yue, Wujin Sun, and Zhen Gu. "Stimuli-responsive nanomaterials for therapeutic protein delivery." Journal of controlled release 194 (2014): 1-19.
Lussier, Danielle M., et al. "Combination immunotherapy with α-CTLA-4 and α-PD-L1 antibody blockade prevents immune escape and leads to complete control of metastatic osteosarcoma." Journal for immunotherapy of cancer 3.1 (2015): 21.
Mitragotri, Samir, Paul A. Burke, and Robert Langer. "Overcoming the challenges in administering biopharmaceuticals: formulation and delivery strategies." Nature reviews Drug discovery 13.9 (2014): 655-672.
Mura, Simona, Julien Nicolas, and Patrick Couvreur. "Stimuli-responsive nanocarriers for drug delivery." Nature materials 12.11 (2013): 991-1003.
Naessens, Myriam, et al. "Dextran dextrinase and dextran of Gluconobacter oxydans." Journal of Industrial Microbiology and Biotechnology 32.8 (2005): 323.
Pardoll, Drew M. "The blockade of immune checkpoints in cancer immunotherapy." Nature Reviews Cancer 12.4 (2012): 252-264.
Prausnitz, Mark R. "Drug delivery: Puncturing cells en masse." Nature materials 14.5 (2015): 470-471.
Prausnitz, Mark R. "Microneedles for transdermal drug delivery." Advanced drug delivery reviews 56.5 (2004): 581-587.
Rogers, Howard W., et al. "Incidence estimate of nonmelanoma skin cancer in the United States, 2006." Archives of dermatology 146.3 (2010): 283-287.
Sharma, Padmanee, and James P. Allison. "Immune checkpoint targeting in cancer therapy: toward combination strategies with curative potential." Cell 161.2 (2015): 205-214.
Simões, M. C. F., J. J. S. Sousa, and A. A. C. C. Pais. "Skin cancer and new treatment perspectives: A review." Cancer letters 357.1 (2015): 8-42.
Sullivan, Ryan J., and Keith T. Flaherty. "Immunotherapy: Anti-PD-1 therapies—a new first-line option in advanced melanoma." Nature reviews Clinical oncology 12.11 (2015): 625.
Sullivan, Sean P., Niren Murthy, and Mark R. Prausnitz. "Minimally invasive protein delivery with rapidly dissolving polymer microneedles." Advanced materials 20.5 (2008): 933-938.
Tao, Peng, et al. "Preparation and optical properties of indium tin oxide/epoxy nanocomposites with polyglycidyl methacrylate grafted nanoparticles." ACS applied materials & interfaces 3.9 (2011): 3638-3645.
Timko, Brian P., et al. "Near-infrared-actuated devices for remotely controlled drug delivery." Proceedings of the National Academy of Sciences 111.4 (2014): 1349-1354.
Tong, Rong, and Robert Langer. "Nanomedicines targeting the tumor microenvironment." The Cancer Journal 21.4 (2015): 314-321.
Topalian, Suzanne L., et al. "Safety, activity, and immune correlates of anti-PD-1 antibody in cancer." New England Journal of Medicine 366.26 (2012): 2443-2454.

(56) References Cited

OTHER PUBLICATIONS

Topalian, Suzanne L., et al. "Survival, durable tumor remission, and long-term safety in patients with advanced melanoma receiving nivolumab." Journal of clinical oncology 32.10 (2014): 1020.

Tumeh, Paul C., et al. "PD-1 blockade induces responses by inhibiting adaptive immune resistance." Nature 515.7528 (2014): 568-571.

Wang, Chao, et al. "Immunological responses triggered by photothermal therapy with carbon nanotubes in combination with anti-CTLA-4 therapy to inhibit cancer metastasis." Advanced materials 26.48 (2014): 8154-8162.

Ye, Yanqi, Jicheng Yu, and Zhen Gu. "Versatile protein nanogels prepared by in situ polymerization." Macromolecular Chemistry and Physics 217.3 (2016): 333-343.

Yu, Jicheng, et al. "Microneedle-array patches loaded with hypoxia-sensitive vesicles provide fast glucose-responsive insulin delivery." Proceedings of the National Academy of Sciences 112.27 (2015): 8260-8265.

Zou, Weiping. "Immunosuppressive networks in the tumour environment and their therapeutic relevance." Nature reviews cancer 5.4 (2005): 263-274.

Extended European Search Report issued for APplication No. 17760691, dated Oct. 2, 2019, 6 pages.

Notice of Reasons for Rejection issued in JP2018-545453 dated Jan. 26, 2021.

First Office Action issued in CN201780019579.8, dated Jan. 14, 2021.

Tai W. et al, "Bio-inspired synthetic nanovesicles for glucose-responsive release of insulin", Biomacromolecules, Sep. 30, 2014, vol. 15, No. 10, pp. 3495-3502.

International Search Report and Written Opinion in PCT/US2017/020135, dated May 11, 2017. 12 pages.

Wang, C. et al. Enhanced Cancer Immunotherapy by Microneedle Patch-Assisted Delivery of Anti-PD1 Antibody, Nano Letters. Mar. 21, 2016, vol. 16, No. 4; pp. 2334-2340.

Yu, Jicheng, et al. Microneedle-array patches loaded with hypoxia-sensitive vesicles provide fast glucose-responsive insulin delivery. Jul. 7, 2015. PNAS, vol. 112, No. 27, 8260-8265.

Office Action, dated Mar. 6, 2023, received in connection with corresponding Canadian Patent Application No. 3,016,313.

* cited by examiner

ENHANCED CANCER IMMUNOTHERAPY BY MICRONEEDLE PATCH-ASSISTED DELIVERY

CROSS REFERENCE TO RELATED APPLICATIONS

This application is a national stage application filed under 35 U.S.C. § 371 of PCT/US2017/020135 filed Mar. 1, 2017, which claims the benefit of U.S. Provisional Patent Application Ser. No. 62/301,789 filed Mar. 1, 2016, the disclosures of which are expressly incorporated herein by reference.

STATEMENT REGARDING FEDERALLY SPONSORED RESEARCH

This invention was made with government support under grant number TR001111 awarded by the National Institutes of Health. The government has certain rights in the invention.

FIELD

The present disclosure relates to microneedle devices and methods for treating a disease (for example, cancer) using a self-degradable microneedle patch for the sustained delivery of an immunotherapeutic agent (for example, an anti-PD1 antibody).

BACKGROUND

Skin cancers are the most common malignancy in humans, particularly among Caucasians. Current estimates suggest that one in five Americans will develop skin cancer in their lifetime (Simões, M. et al. Cancer Lett. 2015, 357, (1), 8-42; Rogers, H. W.; Weinstock, M. et al. Arch. Dermatol. 2010, 146, (3), 283-287). For skin cancer treatment, immunotherapies have been intensively studied over the past several years (Chinembiri, T. N. et al. Molecules 2014, 19, (8), 11679-11721; Pardoll, D. M. Nat. Rev. Cancer 2012, 12, (4), 252-264). Among these studies, checkpoint inhibitors that block the programmed death-1 (PD-1) pathway showed powerful clinical potency (Pardoll, D. M. Nat. Rev. Cancer 2012, 12, (4), 252-264; Gubin, M. M. et al. Nature 2014, 515, (7528), 577-581; Tumeh, P. C. et al. Nature 2014, 515, (7528), 568-571). PD-1 receptors expressed on T cells play a pivotal role in the down regulation of the immune system by triggering inhibitory signaling downstream of T-cell receptor (TCR) and preventing the activation of T-lymphocytes (Pardoll, D. M. Nat. Rev. Cancer 2012, 12, (4), 252-264; Chinai, J. M. et al. Trends Pharmacol. Sci. 2015, 36, (9), 587-595; Gubin, M. M. et al. Nature 2014, 515, (7528), 577-581). The anti-PD-1 antibodies that target the inhibitory receptor have shown striking antitumor activity in phase II and III clinical trials of advanced melanoma (Kyi, C.; Postow, M. A. FEBS Letters 2014, 588, (2), 368-376; Sullivan, R. J.; Flaherty, K. T. Nat. Rev. Clin. Oncol. 2015, 12, (11), 625-626; Topalian, S. L. et al. N. Engl. J. Med. 2012, 366, (26), 2443-2454).

Despite the exciting clinical results of anti-PD-1 antibodies for the treatment of melanoma, the efficacy of the approach remains to be improved. Although much higher compared with the chemotherapy, the long-term durable response rate and overall response rate have the potential to increase (Topalian, S. L. et al. J. Clin. Oncol. 2014, 32, (10), 1020-1030). The cost of treatment is also unsustainably high due to the amount of inhibitors needed. In addition, side effects, such as dosage-dependent autoimmune disorders, have been observed (Topalian, S. L. et al. N. Engl. J. Med. 2012, 366, (26), 2443-2454; Chapman, A. P. Adv. Drug Deliv. Rev. 2002, 54, (4), 531-545; Mitragotri, S.; Burke, P. A.; Langer, R. Nat. Rev. Drug Discovery 2014, 13, (9), 655-72). Thus, there is a need for new devices and methods for improving the delivery and efficacy of immunotherapeutic agents.

SUMMARY

Disclosed herein is an innovative self-degradable microneedle (MN) patch for the sustained delivery of an immunotherapeutic agent (for example, aPD1 (anti-PD1 antibody)) in a physiologically controllable manner.

Disclosed herein is a device for transport of a material across a biological barrier of a subject comprising:
 i) a plurality of microneedles each having a base end and a tip;
 ii) a substrate to which the base ends of the microneedles are attached or integrated; and
 iii) acid-degradable nanoparticles, wherein the nanoparticles encapsulate an immunotherapeutic agent and a pH altering agent.

Also disclosed herein is a method for treating a disease in a subject in need thereof, comprising:
 a) providing a microneedle patch to a subject, wherein the microneedle patch comprises:
  a plurality of microneedles each having a base end and a tip;
  a substrate to which the base ends of the microneedles are attached or integrated;
  acid-degradable nanoparticles, wherein the nanoparticles encapsulate an immunotherapeutic agent and a pH altering agent;
 b) inserting the microneedles into a biological barrier, wherein the pH altering agent decreases the pH within the acid-degradable nanoparticles, and wherein the decrease in the pH degrades the nanoparticle and releases the immunotherapeutic agent into the subject in a controlled-release manner.

In some embodiments, the disease is a cancer. In some embodiments, the cancer is a solid tumor. In one embodiment, the cancer is melanoma.

Also, disclosed herein is a kit of parts for delivering an immunotherapeutic agent across a biological barrier comprising:
 a) a microneedle patch comprising:
  a plurality of microneedles each having a base end and a tip;
  a substrate to which the base ends of the microneedles are attached or integrated; and
 b) acid-degradable nanoparticles, wherein the nanoparticles encapsulate an immunotherapeutic agent and a pH altering agent.

In one embodiment, the acid-degradable nanoparticles comprise modified dextran. In one embodiment, the acid-degradable nanoparticles comprise pH-sensitive dextran nanoparticles. In one embodiment, the pH altering agent is glucose oxidase. In one embodiment, the pH altering agent is glucose oxidase in combination with catalase.

In one embodiment, the nanoparticle further comprises a surfactant. In one embodiment, the surfactant is alginate.

In one embodiment, the microneedles comprise hyaluronic acid.

In one embodiment, the microneedle is comprised of biocompatible hyaluronic acid integrated with pH-sensitive dextran nanoparticles (NPs) that encapsulates an immunotherapeutic agent (for example, aPD1) and glucose oxidase (GOx), which converts blood glucose to gluconic acid. In this embodiment, the generation of acidic environment promotes the self-dissociation of NPs and subsequently results in the substantial release of the immunotherapeutic agent (for example, aPD1). The inventors have identified that even a single administration of the microneedle (MN) patch induces robust immune responses in a B16F10 mouse melanoma model compared to MN without degradation trigger or intratumoral injection of free aPD1 with the same dose. Moreover, this administration strategy can integrate with other immunomodulators (such as anti-CTLA-4) to achieve combination therapy for enhancing anti-tumor efficacy.

Further disclosed herein is a device for transport of a material across a biological barrier of a subject comprising:
  i) a plurality of microneedles each having a base end and a tip;
  ii) a substrate to which the base ends of the microneedles are attached or integrated; and
  iii) acid-degradable nanoparticles, wherein the nanoparticles encapsulate a therapeutic, prophylactic, or diagnostic agent, and a pH altering agent.

BRIEF DESCRIPTION OF THE DRAWINGS

The accompanying figures, which are incorporated in and constitute a part of this specification, illustrate several aspects described below.

DETAILED DESCRIPTION

Figure 1A:
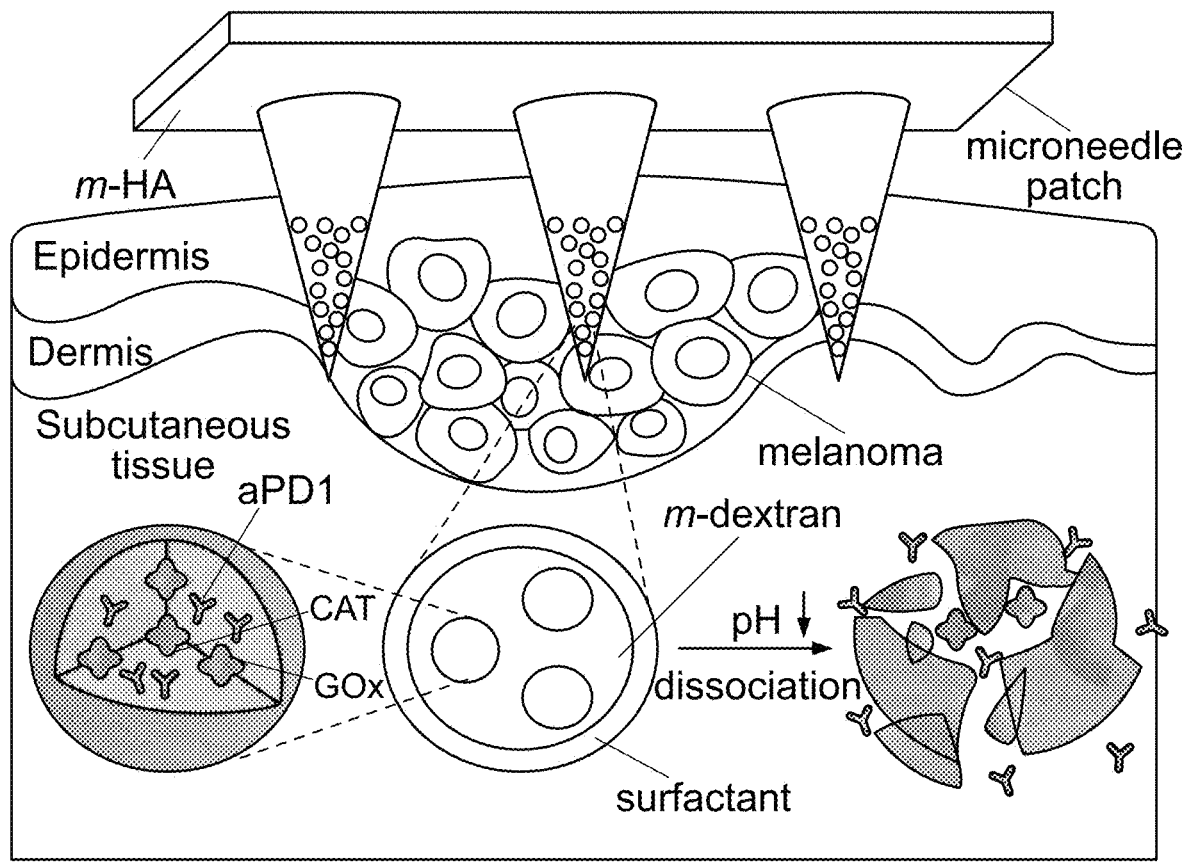
FIGS. 1A-1B show a schematic of the microneedle (MN) patch-assisted delivery of aPD1 for the skin cancer treatment. (a) Schematic of the aPD1 delivered by an MN patch loaded with physiologically self-dissociated nanoparticles (NPs). With GOx/CAT enzymatic system immobilized inside the NPs by double-emulsion method, the enzyme-mediated conversion of blood glucose to gluconic acid promotes the sustained dissociation of NPs, subsequently leading to the release of aPD1. (b) The blockade of PD-1 by aPD1 to activate the immune system to destroy skin cancer cells.

Disclosed herein are devices and methods for the sustained delivery of an immunotherapeutic using a self-degradable microneedle (MN) patch for the sustained delivery of an immunotherapeutic (for example, a PD1 antibody). In one embodiment, the microneedle is comprised of biocompatible hyaluronic acid integrated with pH-sensitive dextran nanoparticles (NPs) that encapsulate an immunotherapeutic and a pH-altering agent. The generation of the acidic environment by the pH altering agent promotes the self-dissociation of NPs and subsequently results in the sustained release of the immunotherapeutic. The inventors have found that even a single administration of the microneedle patch induces a robust immune response when compared to a microneedle without a degradation trigger (for example, a pH-altering agent such as glucose oxidase) or with intratumoral injection of free aPD1 with the same dose of immunotherapeutic agent. In addition, the administration of aPD1 with other immunomodulators (such as anti-CTLA-4) resulted in synergistic anti-tumor efficacy.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this invention belongs. The following definitions are provided for the full understanding of terms used in this specification.

Terminology

Terms used throughout this application are to be construed with ordinary and typical meaning to those of ordinary skill in the art. However, Applicant desires that the following terms be given the particular definition as defined below.

As used in the specification and claims, the singular form "a," "an," and "the" include plural references unless the context clearly dictates otherwise. For example, the term "a cell" includes a plurality of cells, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

"Activities" of a protein, including those relating to "bioactivity," include, for example, transcription, translation, intracellular translocation, secretion, phosphorylation by kinases, cleavage by proteases, and/or homophilic and heterophilic binding to other proteins.

The term "administering" refers to an administration that is oral, topical, intravenous, subcutaneous, transcutaneous, transdermal, intramuscular, intra joint, parenteral, intra-arteriole, intradermal, intraventricular, intracranial, intraperitoneal, intralesional, intranasal, rectal, vaginal, by inhalation or via an implanted reservoir. Administering can be performed using transdermal microneedle-array patches. The term "parenteral" includes subcutaneous, intravenous, intramuscular, intra-articular, intra-synovial, intrasternal, intrathecal, intrahepatic, intralesional, and intracranial injections or infusion techniques.

"Biocompatible" generally refers to a material and any metabolites or degradation products thereof that are generally non-toxic to the recipient and do not cause any significant adverse effects to the subject.

A "composition" is intended to include a combination of active agent and another compound or composition, inert (for example, a detectable agent or label) or active, such as an adjuvant.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purpose. A control can be "positive" or "negative."

As used herein, "conjugated" refers to a non-reversible binding interaction.

As used herein, "displace" refers to interrupting a molecular or chemical interaction between, for example, a protein domain and a peptide, a protein domain and a chemical, a protein domain and a nucleic acid sequence by a chemical, peptide, or nucleic acid having affinity for that specific protein domain than the peptide, chemical, or nucleic acid being displaced.

A "linker" as used herein refers to a molecule that joins adjacent molecules. Generally a linker has no specific biological activity other than to join the adjacent molecules or to preserve some minimum distance or other spatial relationship between them. In some cases, the linker can be selected to influence or stabilize some property of the adjacent molecules, such as the folding, net charge, or hydrophobicity of the molecule.

The terms "peptide," "protein," and "polypeptide" are used interchangeably to refer to a natural or synthetic molecule comprising two or more amino acids linked by the carboxyl group of one amino acid to the alpha amino group of another.

The term "carrier" or "pharmaceutically acceptable carrier" means a carrier or excipient that is useful in preparing a pharmaceutical or therapeutic composition that is generally safe and non-toxic, and includes a carrier that is acceptable for veterinary and/or human pharmaceutical or therapeutic use. As used herein, the terms "carrier" or "pharmaceutically acceptable carrier" encompasses can include phosphate buffered saline solution, water, emulsions (such as an oil/water or water/oil emulsion) and/or various types of wetting agents. As used herein, the term "carrier" encompasses any excipient, diluent, filler, salt, buffer, stabilizer, solubilizer, lipid, stabilizer, or other material well known in the art for use in pharmaceutical formulations and as described further below.

As used herein, the term "polymer" refers to a relatively high molecular weight organic compound, natural or synthetic, whose structure can be represented by a repeated small unit, the monomer (e.g., polyethylene, rubber, cellulose). Synthetic polymers are typically formed by addition or condensation polymerization of monomers. As used herein, the term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

The terms "therapeutically effective amount" or "therapeutically effective dose" refer to the amount of a composition, such as an immunotherapeutic agent, that will elicit the biological or medical response of a tissue, system, animal, or human that is being sought by the researcher, veterinarian, medical doctor or other clinician over a generalized period of time. In some instances, a desired biological or medical response is achieved following administration of multiple dosages of the composition to the subject over a period of days, weeks, or years.

The terms "treat," "treating," "treatment," and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for several days to years prior to the manifestation of symptoms of an infection.

The term "specifically binds," as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

The term "immune checkpoint inhibitor" or "immunotherapeutic" refers to molecules that totally or partially reduce, inhibit, interfere with or modulate one or more checkpoint proteins. Checkpoint proteins regulate T-cell activation or function. Numerous checkpoint proteins are known, such as CTLA-4 and its ligands CD 80 and CD86; and PD1 with its ligands PDL1 and PDL2 (Pardon, Nature Reviews *Cancer* 12: 252-264, 2012). These proteins are responsible for co-stimulatory or inhibitory interactions of T-cell responses. Immune checkpoint proteins regulate and maintain self-tolerance and the duration and amplitude of physiological immune responses. Immune checkpoint inhibitors include antibodies or are derived from antibodies.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the subject, the particular beneficial agent or agents, and the like. Thus, it is not always possible to specify an exact "effective amount." However, an appropriate "effective" amount in any subject case may be determined by one of ordinary skill in the art using routine experimentation. Also, as used herein, and unless specifically stated otherwise, an "effective amount" of a beneficial can also refer to an amount covering both therapeutically effective amounts and prophylactically effective amounts.

An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition. Therapeutically effective and prophylactically effective amounts of a given therapeutic agent will typically vary with respect to factors such as the type and severity of the disorder or disease being treated and the age, gender, and weight of the subject.

The term "therapeutically effective amount" can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

As used herein, the term "pharmaceutically acceptable" component can refer to a component that is not biologically or otherwise undesirable, i.e., the component may be incorporated into a pharmaceutical formulation of the invention and administered to a subject as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

Also, as used herein, the term "pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

As used herein, the term "mixture" can include solutions in which the components of the mixture are completely miscible, as well as suspensions and emulsions, in which the components of the mixture are not completely miscible.

As used herein, the term "subject" can refer to living organisms such as mammals, including, but not limited to humans, livestock, dogs, cats, and other mammals. Administration of the therapeutic agents can be carried out at dosages and for periods of time effective for treatment of a subject. In some embodiments, the subject is a human.

As used herein, the term "controlled-release" or "controlled-release drug delivery" or "sustained-release" refers to release or administration of a drug from a given dosage form in a controlled fashion in order to achieve the desired pharmacokinetic profile in vivo. An aspect of "controlled" drug delivery is the ability to manipulate the formulation and/or dosage form in order to establish the desired kinetics of drug release.

The phrases "concurrent administration", "administration in combination", "simultaneous administration" or "administered simultaneously" as used herein, means that the compounds are administered at the same point in time or immediately following one another. In the latter case, the two compounds are administered at times sufficiently close that the results observed are indistinguishable from those achieved when the compounds are administered at the same point in time.

Microneedle Devices (Patches)

Disclosed herein is an innovative self-degradable microneedle (MN) patch for the sustained delivery of an immunotherapeutic agent (for example, aPD1) in a physiologically controllable manner.

Disclosed herein is a device for transport of a material across a biological barrier of a subject comprising:
 a plurality of microneedles each having a base end and a tip;
 a substrate to which the base ends of the microneedles are attached or integrated; and
 acid-degradable nanoparticles, wherein the nanoparticles encapsulate an immunotherapeutic agent and a pH altering agent.

Also, disclosed herein is a kit of parts for delivering an immunotherapeutic agent across a biological barrier comprising:
 a microneedle patch comprising:
  a plurality of microneedles each having a base end and a tip;
  a substrate to which the base ends of the microneedles are attached or integrated; and
  acid-degradable nanoparticles, wherein the nanoparticles encapsulate an immunotherapeutic agent and a pH altering agent.

In one embodiment, the microneedle is comprised of hyaluronic acid. In one embodiment, the microneedle is comprised of biocompatible hyaluronic acid integrated with pH-sensitive dextran nanoparticles (NPs) that encapsulate aPD1 and glucose oxidase (GOx), which converts blood glucose to gluconic acid. IN this embodiment, the generation of acidic environment promotes the self-dissociation of NPs and subsequently results in the substantial release of aPD1. The inventors have identified that even a single administration of the MN patch induces robust immune responses in a B16F10 mouse melanoma model compared to MN without degradation trigger or intratumoral injection of free aPD1 with the same dose. Moreover, this administration strategy can integrate with other immunomodulators (such as anti-CTLA-4) to achieve combination therapy for enhancing anti-tumor efficacy.

In addition to immunotherapeutic agents, the agent to be delivered to the recipient can also be a therapeutic, prophylactic, or diagnostic agent. For example, the agent can be selected from the group consisting of peptides, proteins, carbohydrates, nucleic acid molecules, lipids, organic molecules, biologically active inorganic molecules, and combinations thereof. For example, a wide range of drugs may be formulated for delivery with the present microneedle devices and methods. As used herein, the terms "drug" or "drug formulation" are used broadly to refer to any prophylactic, therapeutic, or diagnostic agent, or other substance that which may be suitable for introduction to biological tissues, including pharmaceutical excipients and substances for tattooing, cosmetics, and the like. The drug can be a substance having biological activity. The drug formulation may include various forms, such as liquid solutions, gels, solid particles (e.g., microparticles, nanoparticles), or combinations thereof. The drug may comprise small molecules, large (i.e., macro-) molecules, or a combination thereof. In representative, not non-limiting, embodiments, the drug can be selected from among immunologic adjuvants (for example, monophosphoryl lipid A (MPLA), aluminum salt (Alum), CpG oliogodeoxynucleotides (ODN)), amino acids, vaccines, antiviral agents, gene delivery vectors, interleukin inhibitors, immunomodulators, neurotropic factors, neuroprotective agents, antineoplastic agents, chemotherapeutic agents, polysaccharides, anti-coagulants, antibiotics, analgesic agents, anesthetics, antihistamines, anti-inflammatory agents, and viruses. The drug may be selected from suitable proteins, peptides and fragments thereof, which can be naturally occurring, synthesized or recombinantly produced.

In another embodiment, disclosed herein is a device for transport of a material across a biological barrier of a subject comprising:
- a plurality of microneedles each having a base end and a tip;
- a substrate to which the base ends of the microneedles are attached or integrated; and
- acid-degradable nanoparticles, wherein the nanoparticles encapsulate a therapeutic, prophylactic, or diagnostic agent, and a pH altering agent.

In one embodiment, the nanoparticles encapsulate a therapeutic agent and a pH altering agent. In one embodiment, the nanoparticles encapsulate a prophylactic agent and a pH altering agent. In one embodiment, the nanoparticles encapsulate a diagnostic agent and a pH altering agent.

The drug formulation may further include one or more pharmaceutically acceptable excipients, including pH modifiers, viscosity modifiers, diluents, etc., which are known in the art.

In one embodiment, the microneedles comprise hyaluronic acid. In addition to hyaluronic acid, the microneedles may also comprise a variety of materials, including metals, ceramics, semiconductors, organics, polymers, composites, or a combination thereof. Typical materials of construction include pharmaceutical grade stainless steel, gold, titanium, nickel, iron, tin, chromium, copper, palladium, platinum, alloys of these or other metals, silicon, silicon dioxide, and polymers. Representative biodegradable polymers include polymers of hydroxy acids such as lactic acid and glycolic acid polylactide, polyglycolide, polylactide-co-glycolide, and copolymers with PEG, polyanhydrides, poly(ortho)esters, polyurethanes, poly(butyric acid), poly(valeric acid), and poly(lactide-co-caprolactone).

The microneedles should have the mechanical strength to remain intact while being inserted into the biological barrier, while remaining in place for up to a number of days, and while being removed. In some embodiments, the microneedle must remain intact at least long enough for the microneedle to serve its intended purpose (e.g., delivery of the immunotherapeutic agent).

The microneedles can have straight or tapered shafts. In one embodiment, the diameter of the microneedle is greatest at the base end of the microneedle and tapers to a point at the end distal the base. The microneedle can also be fabricated to have a shaft that includes both a straight (untapered) portion and a tapered portion. The needles may also not have a tapered end at all, i.e. they may simply be cylinders with blunt or flat tips.

The microneedles can be oriented perpendicular or at an angle to the substrate. In one embodiment, the microneedles are oriented perpendicular to the substrate so that a larger density of microneedles per unit area of substrate can be provided. An array of microneedles can include a mixture of microneedle orientations, heights, or other parameters.

The microneedles can be formed with shafts that have a circular cross-section in the perpendicular, or the cross-section can be non-circular. For example, the cross-section of the microneedle can be polygonal (e.g. star-shaped, square, triangular), oblong, or another shape. The cross-sectional dimensions can be between about 1 µm and 1000µm, such that the base can be about 100-500 µm, and the tip can be between 1 and 20 µm. In one embodiment, the microneedle can be approximately 300 µm at the base, and approximately 5 µm at the tip.

The length of the microneedles typically is between about 10 µm and 1 mm, preferably between 400 µm and 1 mm. In one embodiment, the length (or height) of the microneedle is about 600µm. The length is selected for the particular application, accounting for both an inserted and uninserted portion. An array of microneedles can include a mixture of microneedles having, for example, various lengths, outer diameters, inner diameters, cross-sectional shapes, and spacings between the microneedles. In one embodiment, the microneedles are arranged in a 15 by 15 array with 600 µm tip-to-tip spacing.

Figure 6:
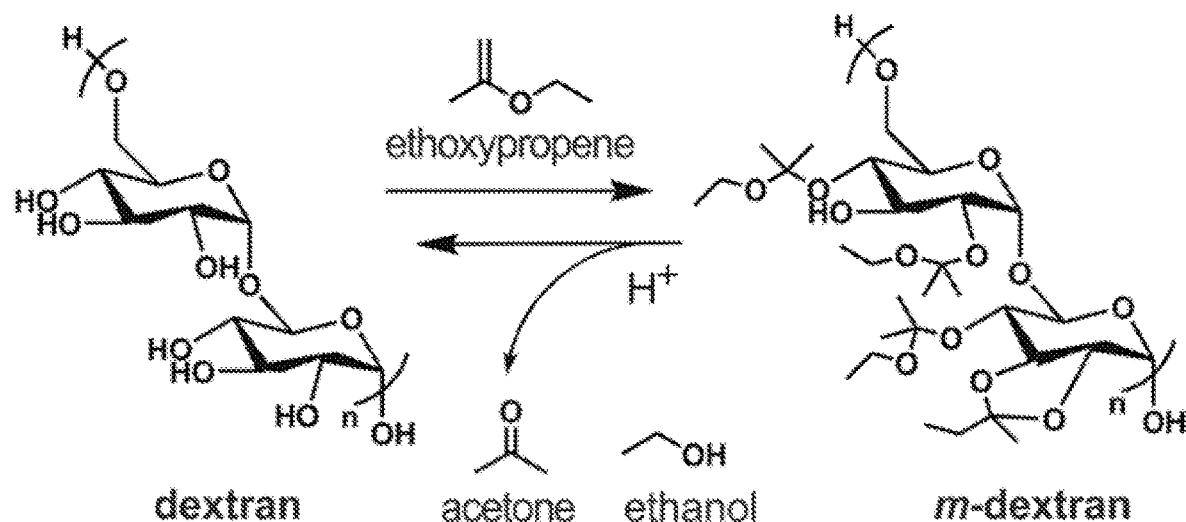
FIG. 6 shows the synthesis and degradation route of modified dextran (m-dextran).

In one embodiment, the acid-degradable nanoparticles comprise modified dextran. In one embodiment, the acid-degradable nanoparticles comprise acetal modified dextran. In one embodiment, the synthesis of modified dextran is shown in FIG. 6.

In one embodiment, the nanoparticle further comprises a surfactant. In one embodiment, the surfactant is alginate.

In one embodiment, the pH altering agent is glucose oxidase (GOx). Glucose oxidase converts blood glucose to gluconic acid. This leads to a decrease in the pH. This decrease in pH then leads to the degradation of the nanoparticle and leads to the sustained-release of the immunotherapeutic agent.

Methods of Treatment

Also disclosed herein is a method for treating a disease in a subject in need thereof, comprising:
- providing a microneedle patch to a subject, wherein the microneedle patch comprises:
  - a plurality of microneedles each having a base end and a tip;
  - a substrate to which the base ends of the microneedles are attached or integrated;
  - acid-degradable nanoparticles, wherein the nanoparticles encapsulate an immunotherapeutic agent and a pH altering agent;
- inserting the microneedles into a biological barrier, wherein the pH altering agent decreases the pH within the acid-degradable nanoparticles, and wherein the decrease in the pH degrades the nanoparticle and releases the immunotherapeutic agent into the subject in a controlled-release manner.

The devices and methods described herein are useful for the treatment of cancers or tumors. In one embodiment, the cancer to be treated is a skin cancer. In one embodiment, the cancer is melanoma.

As contemplated herein, the cancer treated can be a primary tumor or a metastatic tumor. In one aspect, the methods described herein are used to treat a solid tumor, for example, melanoma, lung cancer (including lung adenocarcinoma, basal cell carcinoma, squamous cell carcinoma, large cell carcinoma, bronchioloalveolar carcinoma, bronchogenic carcinoma, non-small-cell carcinoma, small cell carcinoma, mesothelioma); breast cancer (including ductal carcinoma, lobular carcinoma, inflammatory breast cancer, clear cell carcinoma, mucinous carcinoma, serosal cavities breast carcinoma); colorectal cancer (colon cancer, rectal cancer, colorectal adenocarcinoma); anal cancer; pancreatic cancer (including pancreatic adenocarcinoma, islet cell carcinoma, neuroendocrine tumors); prostate cancer; prostate adenocarcinoma; ovarian carcinoma (ovarian epithelial carcinoma or surface epithelial-stromal tumor including serous tumor, endometrioid tumor and mucinous cystadenocarcinoma, sex-cord-stromal tumor); liver and bile duct carcinoma (including hepatocellular carcinoma, cholangiocarcinoma, hemangioma); esophageal carcinoma (including esophageal adenocarcinoma and squamous cell carcinoma); oral and oropharyngeal squamous cell carcinoma; salivary gland adenoid cystic carcinoma; bladder cancer; bladder carcinoma; carcinoma of the uterus (including endometrial adenocarcinoma, ocular, uterine papillary serous carcinoma, uterine clear-cell carcinoma, uterine sarcomas, leiomyosarcomas, mixed mullerian tumors); glioma, glioblastoma, medulloblastoma, and other tumors of the brain; kidney cancers (including renal cell carcinoma, clear cell carcinoma, Wilm's tumor); cancer of the head and neck (including squamous cell carcinomas); cancer of the stomach (gastric cancers, stomach adenocarcinoma, gastrointestinal stromal tumor); testicular cancer; germ cell tumor; neuroendocrine tumor; cervical cancer; carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, myofibroblastoma, fibromatosis, inflammatory myofibroblastic tumor, lipoma, angiolipoma, granular cell tumor, neurofibroma, schwannoma, angiosarcoma, liposarcoma, rhabdomyosarcoma, osteosarcoma, leiomyoma, leiomysarcoma, skin, including melanoma, cervical, retinoblastoma, head and neck cancer, pancreatic, brain, thyroid, testicular, renal, bladder, soft tissue, adenal gland, urethra, cancers of the penis, myxosarcoma, chondrosarcoma, osteosarcoma, chordoma, malignant fibrous histiocytoma, lymphangiosarcoma, mesothelioma, squamous cell carcinoma; epidermoid carcinoma, malignant skin adnexal tumors, adenocarcinoma, hepatoma, hepatocellular carcinoma, renal cell carcinoma, hypernephroma, cholangiocarcinoma, transitional cell carcinoma, choriocarcinoma, seminoma, embryonal cell carcinoma, glioma anaplastic; glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, pheochromocytoma, Islet cell carcinoma, malignant carcinoid, malignant paraganglioma, melanoma, Merkel cell neoplasm, cystosarcoma phylloide, salivary cancers, thymic carcinomas, and cancers of the vagina among others.

Immunotherapeutic Agents (Immune Checkpoint Inhibitors) and Immunologic Adjuvants There are a number of immunotherapeutic agents that are known to inhibit immune checkpoint proteins (immune checkpoint inhibitors). Known immune checkpoint proteins include CTLA-4, PD1 and its ligands PD-L1 and PD-L2 and in addition LAG-3, BTLA, B7H3, B7H4, TIM3, KIR. The pathways involving LAG3, BTLA, B7H3, B7H4, TIM3, and KIR are recognized in the art to constitute immune checkpoint pathways similar to the CTLA-4 and PD-1 dependent pathways (see e.g. Pardoll, 2012. Nature Rev Cancer 12:252-264).

An immune checkpoint inhibitor is any compound inhibiting the function of an immune checkpoint protein. Inhibition includes reduction of function and/or full blockade. In one embodiment, the immune checkpoint protein is a human immune checkpoint protein. Thus, the immune checkpoint protein inhibitor can be an inhibitor of a human immune checkpoint protein. Immune checkpoint proteins are described in the art (see for example, Pardoll, 2012. Nature Rev. Cancer 12: 252-264).

Preferred immune checkpoint protein inhibitors are antibodies that specifically recognize immune checkpoint proteins. A number of PD1, PDL-1, PD-L2, CTLA-4, LAG-3, BTLA, B7H3, B7H4, 4-1BB (CD137), TIM3 and KIR inhibitors are known and in analogy of these known immune checkpoint protein inhibitors, alternative immune checkpoint inhibitors may be administered using the devices and methods disclosed herein.

Examples of PD-1 inhibitors include without limitation humanized antibodies blocking human PD-1 such as pembrolizumab (formerly lambrolizumab), or pidilizumab as well as fully human antibodies such as nivolumab (previously known as MDX-1106 or BMS-936558). Ipilimumab is a fully human CTLA-4 blocking antibody presently marketed under the name Yervoy (Bristol-Myers Squibb). A second CTLA-4 inhibitor is tremelimumab. In one embodiment, the immunotherapeutic is nivolumab.

In addition, immune checkpoint inhibitors may include without limitation humanized or fully human antibodies blocking PD-L1 such as MEDI-4736 (disclosed in WO2011066389 A1), MPDL328 OA (disclosed in U.S. Pat. No. 8,217,149 B2) and MIH1 (Affymetrix obtainable via eBioscience (16.5983.82)) and other PD-L1 inhibitors presently under investigation. Additional antibodies to PD-L1 include atezolizumab and durvalumab.

In one embodiment, KIR inhibitors are administered. Lirilumab is a human monoclonal antibody that binds to KIR2DL1/2L3. In one embodiment, inhibitors of 4-1BB (CD137) are administered. Urelumab targets the extracellular domain of CD137.

In one embodiment, an immune checkpoint inhibitor is preferably selected from a CTLA-4, PD-1 or PD-L1 inhibitor, such as selected from the known CTLA-4, PD-1 or PD-L1 inhibitors mentioned above (ipilimumab, tremelimumab, pembrolizumab, nivolumab, atezolizumab, durvalumab, AMP-244, MEDI-4736, MPDL328 OA, MIH1), or combinations thereof.

The selection of an immune checkpoint inhibitor from PD1 and PD-L1 inhibitors, such as a known PD-1 or PD-L1 inhibitor mentioned above, is more preferred and most preferably a selection is made from a PD-1 inhibitor, such as a known PD1 inhibitor mentioned above. In preferred embodiments, the PD1 inhibitor is nivolumab or pembrolizumab or another antagonist antibody against human PD1.

In one embodiment, the immunotherapeutic agent can be administered in combination with an immunological adjuvant. An immunologic adjuvant is any substance that acts to accelerate, prolong, or enhance immune responses when used in combination with other immunotherapeutic agents (for example, monophosphoryl lipid A (MPLA), aluminum salt (Alum), unmethylated CpG dinucleotide-containing DNA) (See Lim, Y T. Clin Exp Vaccine Res. 2015 January; 4(1): 54-58).

EXAMPLES

The following examples are set forth below to illustrate the compositions, devices, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Enhanced Cancer Immunotherapy by Microneedle Patch-Assisted Delivery of Anti-PD1 Antibody Materials All chemicals were obtained from commercial sources and used without further purification. Sodium hyaluronic acid (the molecular weight of 300 kDa) was purchased from Freda Biochem Co., Ltd. (Shandong, China). Alginate (Mn=160 kDa), dextran (Mn=9-11 kDa), glucose oxidase (GOx) and bovine catalase (CAT) were purchased from Sigma-Aldrich. 2-Ethoxy-1-propene was obtained from Synthonix Inc. The deionized water was prepared by a Millipore NanoPure purification system (resistivity higher than 18.2 MΩ·cm-1). All the organic solvents for synthesis and analysis were ordered from Fisher Scientific Inc. and used as received.

Cell Lines

The mouse melanoma cell line B16F10 was purchased from the American Type Culture Collection. For bioluminescent in vivo tumor imaging, B16F10-luc cells were gifts from Dr. Leaf Huang at UNC. The cells were maintained in Dulbecco's Modified Eagle Medium (Gibco, Invitrogen) supplemented with 10% fetal bovine serum (Invitrogen, Carlsbad, CA), 100 U/mL penicillin (Invitrogen) and 100 U/mL streptomycin (Invitrogen). RAW 264.7 murine macrophages was purchased from the American Type Culture Collection and maintained in RPMI 1640 Medium (Gibco, Invitrogen) supplemented with 10% fetal bovine serum (Invitrogen, Carlsbad, CA), 100 U/mL penicillin (Invitrogen) and 100 µg/mL streptomycin (Invitrogen).

Antibodies aPD1 (anti-PD1 antibody) and aCTLA4 (anti-CTLA4 antibody) used in vivo were purchased from Biolegend Inc. Dosing per injection was 1 mg/kg. Staining antibodies included CD3, CD4, and CD8 for FACS and were analyzed following manufacturers' instructions. Stained cells were analyzed on a Calibur FACS instrument (BD), and were analyzed using flowjo software.

Synthesis and Characterizations of Acrylate Modified HA (m-HA)

m-HA was synthesized following the literature (Lee, D.-K. et al. *ACS Nano* 2015, 9, (11), 11490-11501). Briefly, 1.0 g of HA was dissolved in 50 mL of DI water at 4° C., to which 0.8 mL of methacrylic anhydride (MA) was added dropwise. The reaction solution was adjusted to pH 8-9 by the addition of 5N NaOH and stirred at 4° C. for 24 h. The resulting polymer was obtained by precipitation in acetone, followed by washing with ethanol 3 times. The product was re-dissolved in DI water and the solution dialysed against DI water for 2 days. m-HA was achieved by lyophilization with a yield of 87.5%. The degree of modification was calculated to be 15% by comparing the ratio of the areas under the proton peaks at 5.74 and 6.17 ppm (methacrylate protons) to the peak at 1.99 ppm (N-acetyl glucosamine of HA) after performing a standard deconvolution algorithm to separate closely spaced peaks.

m-HA: $^1$H NMR (D$_2$O, 300 MHz, δ ppm): 1.85-1.96 (m, 3H, CH2=C(CH$_3$)CO), 1.99 (s, 3H, NHCOCH$_3$), 5.74 (s, 1H, CH$^1$H$^2$=C(CH$_3$)CO), 6.17 (s, 1H, CH$^1$H$^2$=C(CH$_3$)CO).

Synthesis and Characterizations of Pendant Acetal Modified Dextran (m-Dextran)

Briefly, 1.0 g of dextran (molecular weight: 9-11 kDa) was added to flame-dried flask and purged with argon. 10 mL of anhydrous DMSO was added and stirred until the dextran was completely dissolved. Pyridinium p-toluenesulfonate (PPTS, 15.6 mg, 0.062 mmol) was added to the solution followed by 2-ethoxypropene (4.16 mL, 37 mmol). The mixture was purged with argon and then sealed to prevent reactant evaporation. The reaction was stirred at room temperature for 30 min, and then was quenched with 1 mL of triethylamine. The resulting mixture was precipitated and washed three times in basic water (pH~8) to prevent degradation and collected by centrifugation (8000 rpm, 15 min). Residual water was removed by lyophilization. m-dextran: $^1$H NMR (DMSO-d$_6$, 300 MHz, δ ppm): 1.10 (m, OCH$_2$CH$_3$), 1.30 (m, C(CH$_3$)$_2$), 3.40 (m, OCH$_2$CH$_3$), 3.55-3.85 (br, dextran C$_2$—H~C$_6$—H), 4.88 (br, dextran Preparation of Nanoparticles Nanoparticles were prepared by an improved double emulsion (water-in-oil-in-water) solvent evaporation/extraction method. Briefly, 1 mL of organic phase (dichloromethane (DCM)) containing 25 mg of m-dextran was emulsified with 0.5 mL of aqueous phase containing 0.25 mg of anti-PD-1 and anti-CTLA-4 antibody only or together with 1.25 mg of enzymes (weight ratio of glucose oxidase to catalase 4:1) by sonication for 45 cycles (1 s each with a duty cycle of 45%). Thereafter, the primary emulsion was immediately poured into 25 mL of the alginate aqueous solution (1%) and sonicated for 45 cycles. The double emulsion was subsequently transferred into 150 mL of alginate aqueous solution (0.2%). The mixed suspension was stirred at room temperature to eliminate DCM by evaporation. After 2 h, the resulting nanoparticles were cleaned and collected by repeating a procedure of centrifuging at 10,000 rpm and suspending in distilled water three times. The final weight ratio of m-dextran/anti-PD-1 antibody/enzymes for preparation of double emulsion was determined as 100/1/5. Particles containing fluorescein isothiocyanate (FITC) labeled antibody were made in the same manner as above.

The loading capacity (LC) and encapsulation efficiency (EE) of antibody-encapsulated nanoparticles were determined by measuring the amount of non-encapsulated IgG through mouse monoclonal antibody ELISA assay and using empty particles as basic correction. LC and EE were calculated as LC=(A−B)/C, EE=(A−B)/A, where A was expected encapsulated amount of antibody, B was the free amount of antibody in the collection solution, and C was the total weight of the particles. Particle size and polydispersity intensity were measured by dynamic light scattering (DLS). The zeta potential of the NPs was determined by their electrophoretic mobility using the same instrument after appropriate dilution in DI water. Measurements were made in triplicate at room temperature.

Nanoparticles (NP) morphology was investigated by scanning electron microscopy. Particles were suspended in deionized water at concentration of 0.5 mg/mL and the resulting dispersions were dripped onto silicon wafers and allowed to air dry under room temperature overnight. The particles were then sputter coated with gold/palladium and imaged. The images were captured by a JEOL 6400F SEM (Tokyo, Japan), operating at 20 kV.

Fabrication and Characterization of Nanoparticle-Loaded Microneedles

All of the MNs in this study were fabricated using six uniform silicone molds from Blueacre Technology Ltd. machined by directly laser ablation to create arrays of cylindrical holes. Each microneedle had a 300 µm by 300 µm round base tapering to a height of 600 µm with a tip radius of around 5 µm. The microneedles were arranged in a 15 by 15 array with 600 µm tip-to-tip spacing.

After preparation of the nanoparticles, the prepared nanoparticles were dispersed in 0.6 mL distilled water in a bath sonicator for 1 min. Then, 50 uL of NPs suspension (containing 2 mg of NPs) was directly deposited by pipetting onto each silicone micromold surface followed by vacuum (600 mmHg) condition for 5 min to allow the NP solution flow into the microneedle cavities. Afterward, the micromolds were transferred to a Hettich Universal 32R centrifuge for 20 min at rpm=2000 to compact NPs into microneedle cavities. The deposition process was repeated for total five times and the residue NPs on the mold surface during the fabrication were removed to get rid of any undesired results. For better microneedles morphology, a piece of 4 cm×9 cm silver adhesive tape was applied around the 2 cm×2 cm micromold baseplate. In addition, 3 mL premixed m-HA (4 wt %) with N,N'-methylenebisacrylamide (MBA, 4 wt %) and photo initiator (Irgacure 2959, 0.05 wt %) solution was added to the prepared micromold reservoir. The final device underwent 6-8 hours of drying at 25° C. in a vacuum dessicator. After desication was completed, the microneedle arrays were carefully separated from the silicone mold and were exposed to UV light (wavelength: 320-450 nm) for 30 s. The needle base can be tailored to fit the injection syringe. The resulting product can be stored in a sealed six well container for up to 30 days. The fluorescent microneedle were fabricated with FITC labeled nanoparticle and Rhodamine B labeled m-HA. The morphology of the microneedles was characterized on a FEI Verios 460L field-emission scanning electron microscope (FESEM) at the Analytical Instrumentation Facility at North Carolina State University. The fluorescence images of MNs were taken by Olympus IX70 multi-parameter fluorescence microscope. The UV crosslinking process was conducted using Dymax BlueWave 75 UV Curing Spot Lamp.

Mechanical Strength Test

The mechanical strength measurements of MNs have been conducted under ambient and isometric test conditions on a tensile load frame. The tensile force was continuously monitored as a stainless steel plate compressing arrays of microneedles along the y-direction on a stress-strain gauge. The initial gauge was set at 2.00 mm between the MN tips and the stainless steel plate, 10.00 N as load cell capacity. The speed of the top stainless steel plate movement towards the MN-array patch was 0.1 mm/s. The failure force of MNs was recorded as the needle began to buckle.

Skin Penetration Efficiency Test

The MN-array was applied to the dorsum of the mouse for 30 min and removed. The mouse was euthanized and the skin sample was embedded in OCT compound (Sakura Finetek) and flash-frozen in an isopentane bath on dry ice. The frozen tissues were sectioned (10-µm thickness), mounted on microscope slides, and stored at −80° C. Fluorescence micrographs of skin histological section after insertion of FITC labeled microneedles were taken by Olympus IX70 multi-parameter fluorescence microscope. The sample was hematoxylin and eosin (H&E) stained in the Histology Laboratory at NC State College of Veterinary Medicine. In a separate experiment, sites of excited skin were stained by trypan blue for 5 min before imaging. After wiping off residual dye from the skin surface with dry tissue paper, the skin sample was viewed by optical microscopy (Leica EZ4 D stereo microscope).

In Vitro Antibody Release Studies from MNs

In vitro release of antibody from MNs was evaluated through incubation of MN patches in 2 mL PBS buffer (NaCl, 137 mM; KCl, 2.7 mM; $Na_2HPO_4$, 10 mM; $KH_2PO_4$, 2 mM; pH 7.4) at 37° C. in a 6 well plate on an orbital shaker. Various amounts of glucose were added to each tube to reach a final glucose concentration (0 mg/dL, 100 mg/dL). At the predetermined times, 25 µL of the sample was removed for analysis and 25 µL of fresh release media was then added to the well to maintain a constant volume and placed back within the incubator. The pH value of the sample was recorded by the pH meter (Fisher Scientific, AB15), and then the total antibody content was examined using ELISA. The absorbance of each well was detected in a UV-Vis spectrophotometer at 450 nm, and the concentration was interpolated from an antibody standard curve.

Cytotoxicity Study

Cytotoxicity study toward MNs was performed using B16F10 cells. Cells were seeded into 96-well plates at a density of 5,000 cells per well and cultivated in 100 µL of Dulbecco's Modified Eagle Medium (DMEM, 25 mM glucose) with 10% fetal bovine growth serum (FBS), 1× Pen-Strep, 1× L-Glutamine and 2.5 µL of Beta Mercaptoethanol (Biorad, Hercules, CA, USA) per 500 mL media. The plates were then incubated in 5% $CO_2$ at 37° C. for 12 h to reach 70-80% confluency before addition of serial dilutions of the releasing media incubated with empty MNs. After incubation with MNs for 24 h, the cells were washed with PBS solution and incubated with 100 µL of fresh FBS free DMEM and 20 µL of freshly prepared 3-(4,5-dimethylthiazol-2-yl)-2,5-diphenyltetrazolium bromide solution (MTT solution, 5 mg/mL). The plates were incubated for an additional 4 h. After 4 h, the solution was carefully removed and then followed by the addition of 150 µL dimethyl sulfoxide (DMSO). The absorbance of the plates was read at 590 nm and a reference wavelength of 620 nm using a microplate reader (Infinite M200 Pro, Tecan, Morrisville, NC, USA) within 10 min.

Mice and In Vivo Tumor Models

Female C57B6 mice were purchased from Jackson Lab (USA). All mouse studies were performed in the context of an animal protocol approved by the Institutional Animal Care and Use Committee at North Carolina State University and University of North Carolina at Chapel Hill. Mice were weighed and randomly divided into different groups. 10 d after 1×10$^6$ luciferase-tagged B16F10 tumor cells transplanted into the back of mice (the tumor reaches ~50-60 $mm^3$), aPD1 (1 mg/kg) were administered into mice by intratumoral/intravenous injection or by microneedle. The tumor growth was monitored by bioluminescence signals of B16F10 cells. Tumors were also measured by digital caliper. The tumor volume ($mm^3$) was calculated as (long diameter× short diameter$^2$)/2

In Vivo Bioluminescence and Imaging

Bioluminescence images were collected with a Xenogen IVIS Spectrum Imaging System. Living Image software (Xenogen) was used to acquire the data 10 min after intraperitoneal injection of d-luciferin (Pierce) in DPBS (15 mg/ml) into animals (10 µL/g of body weight).

Confocal Microscopy

Tumors were dissected from the mice and snap frozen in optimal cutting medium (O.C.T.). Several micrometer sections were cut using a cryotome and mounted on slides. Sections were fixed in ice-cold acetone for 10 minutes prior to rehydration with PBS. After blocking with BSA (3%), sections were stained with primary antibodies overnight at 4° C. Slides were analyzed using a confocal microscope (Zeiss).

ELISA

To test the bioactivity of aPD1, total aPD1 was extracted from MN patches at different time points for ELISA assay. Corning Costar 9018 ELISA plate was coated with purified mouse PD1 protein in PBS. The plate was sealed and incubated overnight at 4° C. After washing and blocking, the samples of aPD1 were added into wells at room temperature for 2 hours. After washing with washing buffer, HRP-conjugated anti-rat lg(H+L) mAbs were added into wells at room temperature for 1 hour followed with washing. TMB substrate solution was added for the detection of bioactivity of aPD1.

Statistical Analysis

Statistical analysis was evaluated using GraphPad Prism (5.0). Statistical significances were calculated with the paired Student t test and two-way ANOVA. P values of 0.05 or less were considered significant.

Results

Figure 1B:
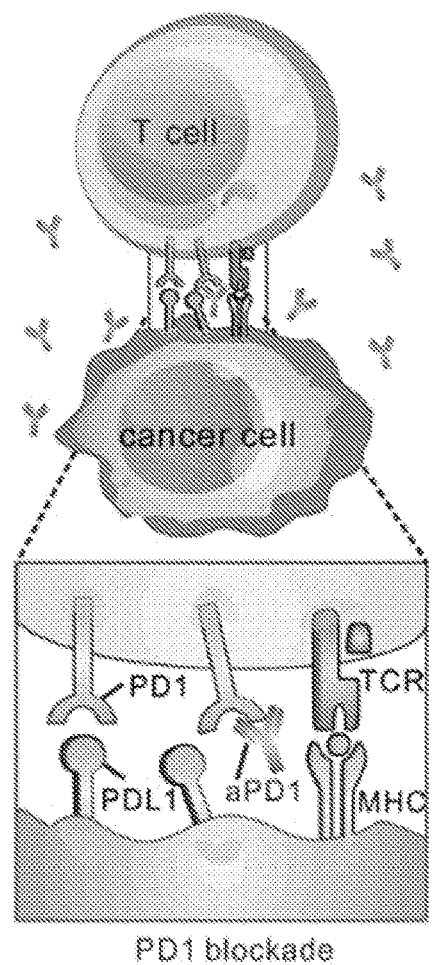

Disclosed in this example, is a physiologically self-degradable MN patch-assisted cancer immunotherapy for controlled delivery of aPD1 toward melanoma (FIG. 1). MNs have been widely explored in transdermal drug delivery during the last decade (Chiappini, C. et al. *Nat. Mater.* 2015; Yu, J. et al. *Proc. Natl. Acad. Sci. U.S.A.* 2015, 112, (27), 8260-8265; Sullivan, S. P. et al. *Adv. Mater.* 2008, 20, (5), 933-938; Prausnitz, M. R. *Adv. Drug Deliv. Rev.* 2004, 56, (5), 581-587; Lee, D.-K. et al. *ACS Nano* 2015, 9, (11), 11490-11501). The skin is an active protective barrier serving as immune surveillance system. MNs can painlessly pierce into the immune-cell-rich epidermis and deliver aPD1 to regional lymph and capillary vessels, promoting its interaction with T cells (Harvey, A. J. et al. *J. Pharm. Res.* 2010, 28, (1), 107-116). With the aim of enhancing retention of aPD1 in the tumor microenvironment, providing enzyme-mediated sustained drug release, allowing facile combination with other therapeutics, MNs were integrated with pH-sensitive dextran NPs (Lu, Y. et al. *J. Control Release* 2014, 194, 1-19). Each MN is comprised of biocompatible hyaluronic acid (HA) integrated with NPs that encapsulate aPD1 and glucose oxidase (GOx). GOx is applied to convert blood glucose to gluconic acid in the presence of oxygen ($O_2$). Catalase (CAT) assists glucose oxidation by regeneration of $O_2$ and helps consume undesired hydrogen peroxide ($H_2O_2$):

Glucose + $O_2$ + $H_2O$ $\xrightarrow{GOx}$ Gluconic Acid + $H_2O_2$.

With GOx/CAT enzymatic system immobilized inside the NPs, the enzyme-mediated generation of gluconic acid promotes the gradual self-dissociation of NPs and results in the sustained release of aPD1 over a three-day administration period (Mura, S. et al. *Nat. Mater.* 2013, 12, (11), 991-1003; Chen, Q. et al. *Biomaterials* 2015, 73, 214-230). A single administration of the MN patch induces robust immune responses in B16F10 mouse melanoma model exceeding MN in absence of the trigger element (pH altering agent) (GOx) or intratumor injection of free aPD1. Additionally, MN severs as a platform for combined therapy with other immunomodulators to enhance immunotherapy efficiency. These results demonstrate that the MN patch-assisted system provides an innovative delivery strategy of aPD1 via a simple and safe technique that improves cancer immunogenicity and facilitates the clinical treatment of melanoma.

Figure 2A:
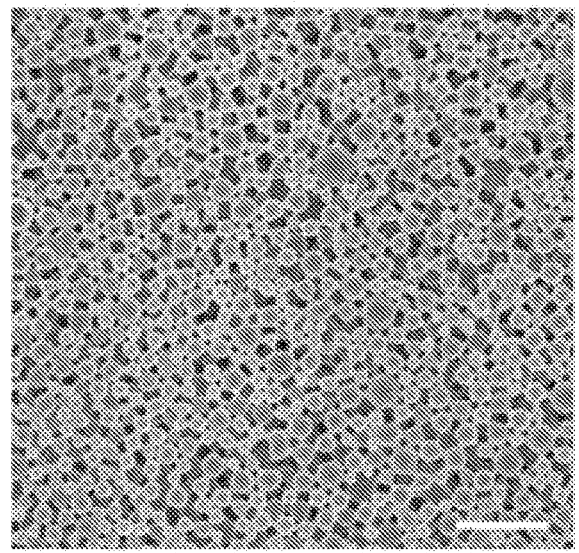
FIGS. 2A-2F show the characterization of aPD1 loaded microneedles. (a) SEM image of NPs (Scale bar: 1000 nm). (b) The average hydrodynamic sizes determined by DLS. (c) SEM image of MN patch (Scale bar: 200 μm). (d) Higher magnification of SEM imaging of MN apex confirmed that the MN was loaded with NPs (Scale bar: 5 μm). (e) Fluorescence imaging of a representative MN patch that contained FITC-antibody loaded NPs (Scale bar: 200 μm). (f) Mechanical property of the MN. The failure force for desired MN was quantitatively measured as 0.38 N/needle.
Figure 2B:
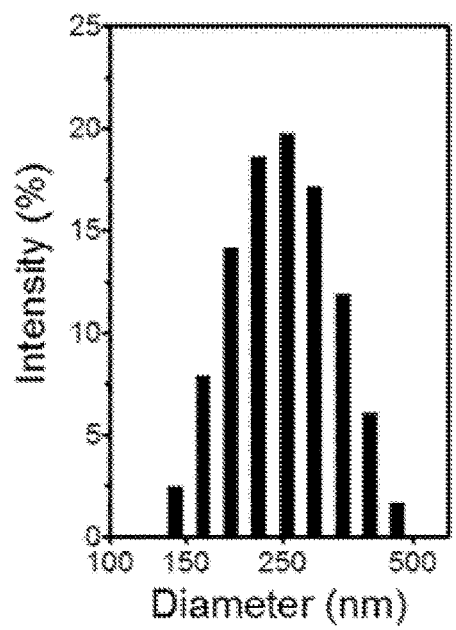
Figure 7:
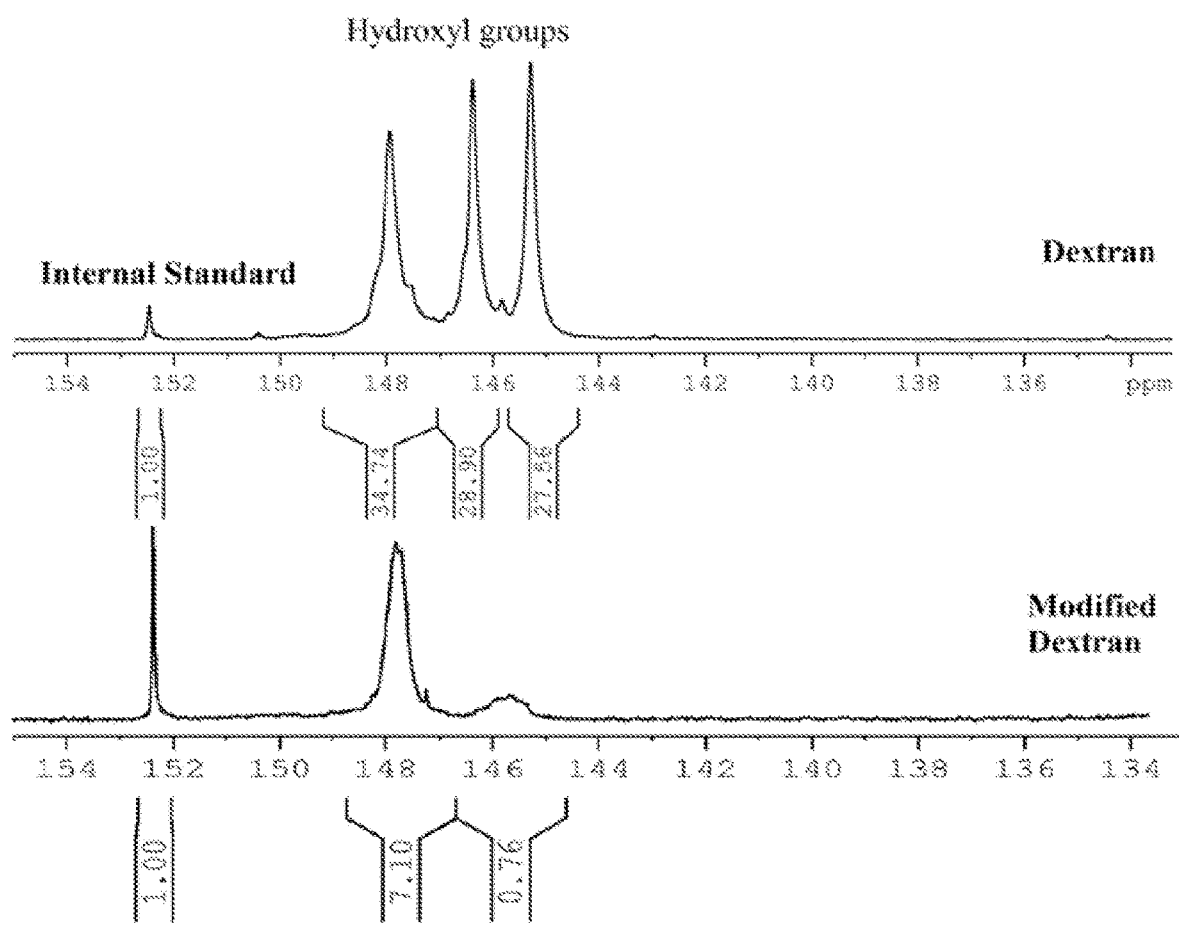
FIG. 7 shows nuclear magnetic resonance (NMR) of modified dextran.
Figure 8:
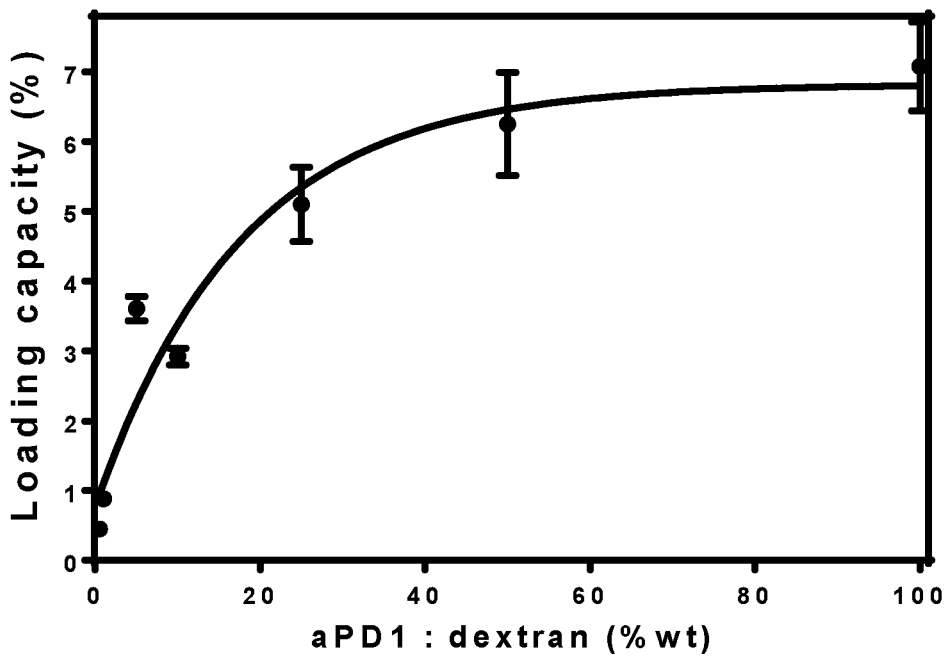
FIG. 8 shows loading capacity of aPD1 at different weight ratio between aPD1 and dextran.

The self-dissociated nanoparticles (NPs) were comprised of four components: acid-degradable polymeric matrix, polyelectrolyte-based surfactant, GOx/CAT enzymatic system, and aPD1. Native dextran is fully biocompatible, biodegradable, widely available, and easy to modify, and was chosen as the matrix component of the NPs (Naessens, M. et al. *J. Ind. Microbiol. Biotechnol.* 2005, 32, (8), 323-334). Ethoxypropene was conjugated to dextran via an acid-catalyzed reaction, which rendered the derived dextran (designated m-dextran) with 89% substitution of hydroxyl to pendant acetals (FIGS. 6, 7) (Bachelder, E. M. et al. *J. Am. Chem. Soc.* 2008, 130, (32), 10494-10495; Gu, Z. et al. *ACS Nano* 2013, 7, (5), 4194-4201). The m-dextran was soluble in organic solvents and enabled the encapsulation of aPD1 during the formation of NPs in a double emulsion process (Gu, Z. et al. G. *ACS Nano* 2013, 7, (5), 4194-4201). An anionic polysaccharide, alginate, was further incorporated as surfactant to form a negatively charged surface coating. As depicted in the scanning electron microscopy (SEM) images (FIG. 2A), the resulting NPs had spherical shapes with mono-disperse particle sizes. The average hydrodynamic sizes determined by dynamic light scattering (DLS) were 250 nm (FIG. 2b). The NPs had an antibody loading capacity of 7.1 wt %, without significant leakage of antibody or obvious morphological change at 4° C. for 3 weeks (FIG. 8).

Figure 2C:
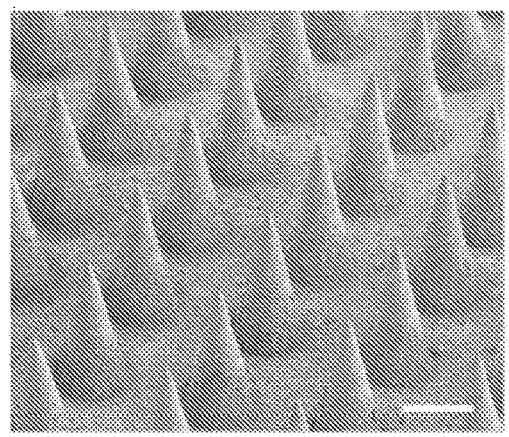
Figure 2D:
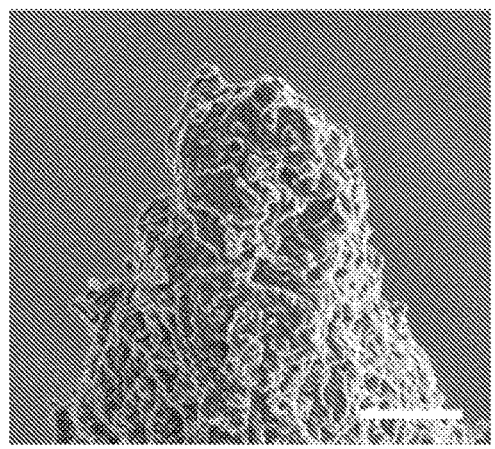
Figure 2E:
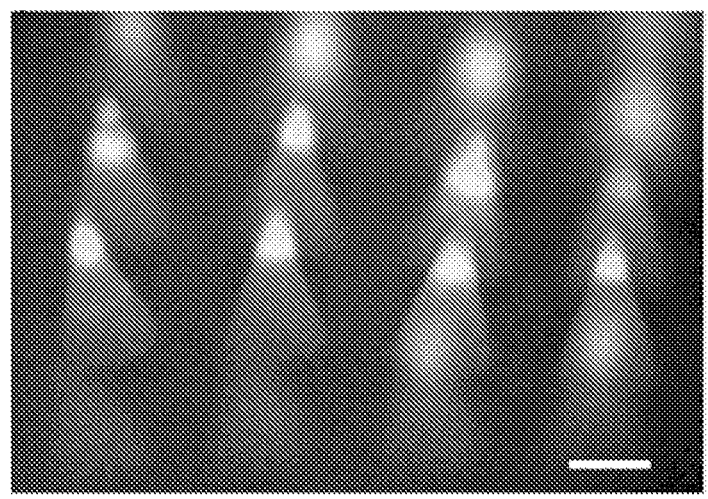
Figure 2F:
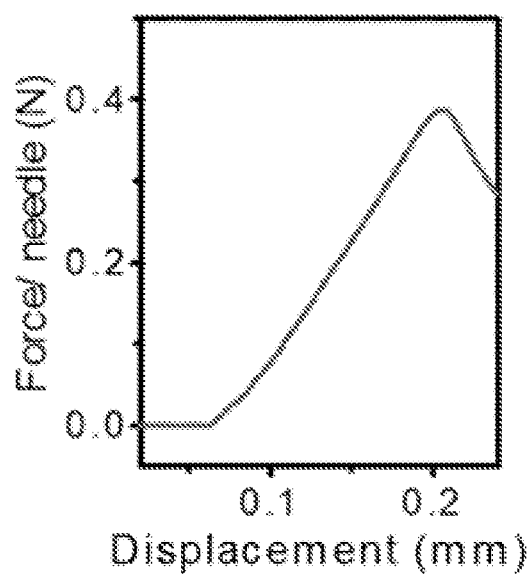
Figure 3A:
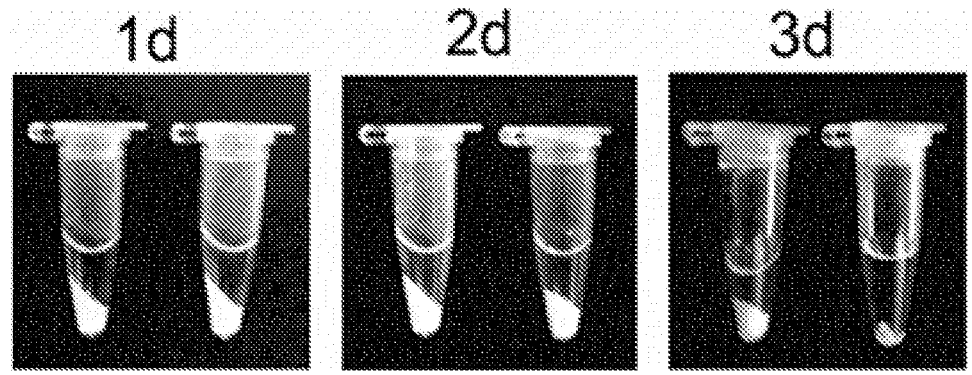
FIGS. 3A-3E show in vitro studies of the nanoparticles (NPs) loaded-microneedle (MN) patch. (a) Pictures of the self-dissociated NPs incubated in PBS (left) or 100 mg/dL (right) glucose solution at 37° C. over time. (b) SEM images of NP morphology change before (left) and after (right) incubation in 100 mg/dL glucose solution for three days. (Scale bar: 100 nm) (c) Relevant pH changes of MNs incubated in 100 mg/dL glucose solution at 37° C. over time. Equilibrium was reached after the swelling of MNs in the first 10 minutes when incubated in the solution. (d) UV absorbance of NP suspensions in 96 well plates at $A_{400}$ nm. (e) In vitro accumulated aPD1 release from the MN patches incubated in 100 mg/dL glucose solution at 37° C. over time. The error bars are based on the standard deviation (SD) of the samples (n=3).
Figure 3B:
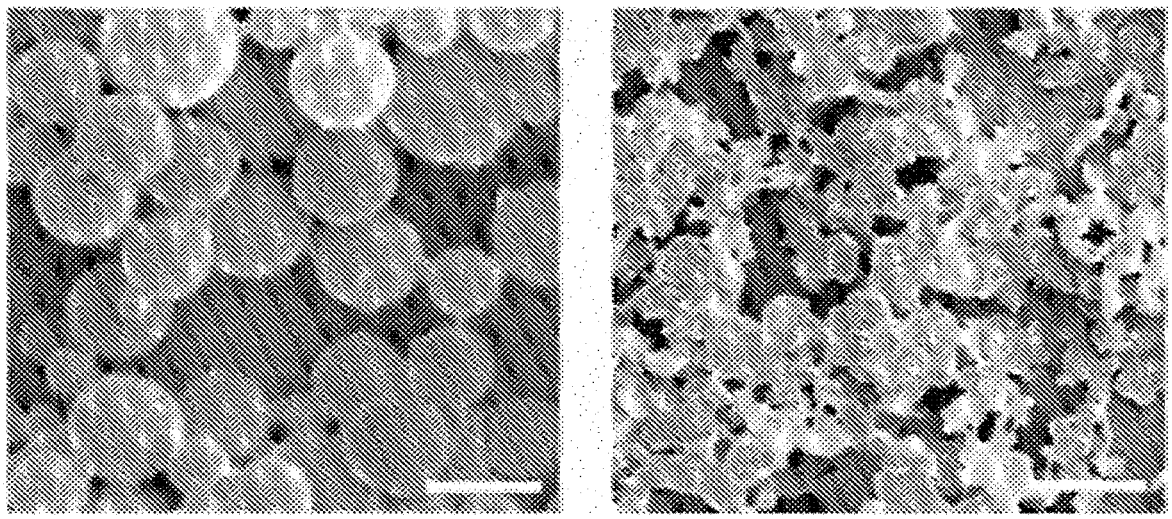
Figure 3C:
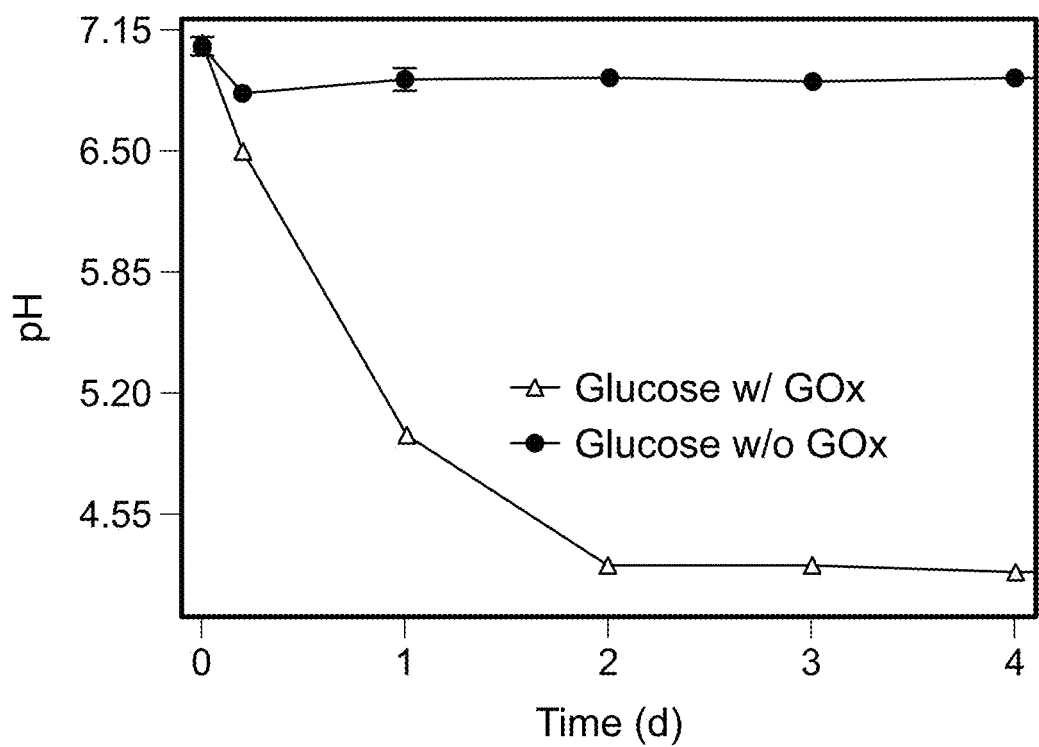
Figure 3D:
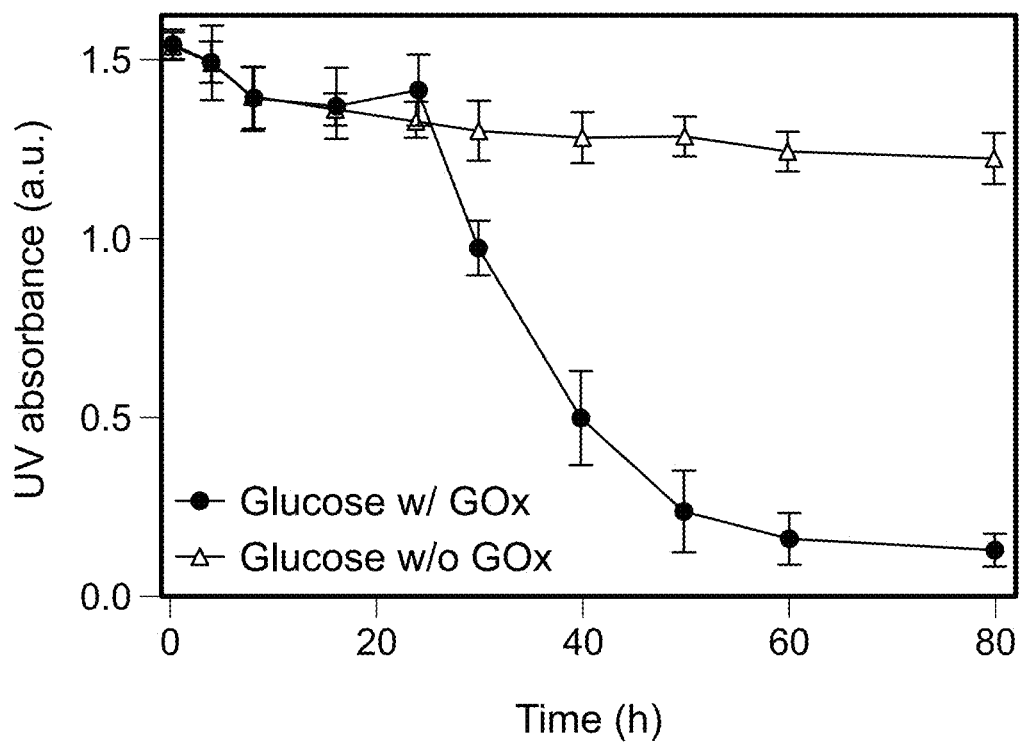
Figure 3E:
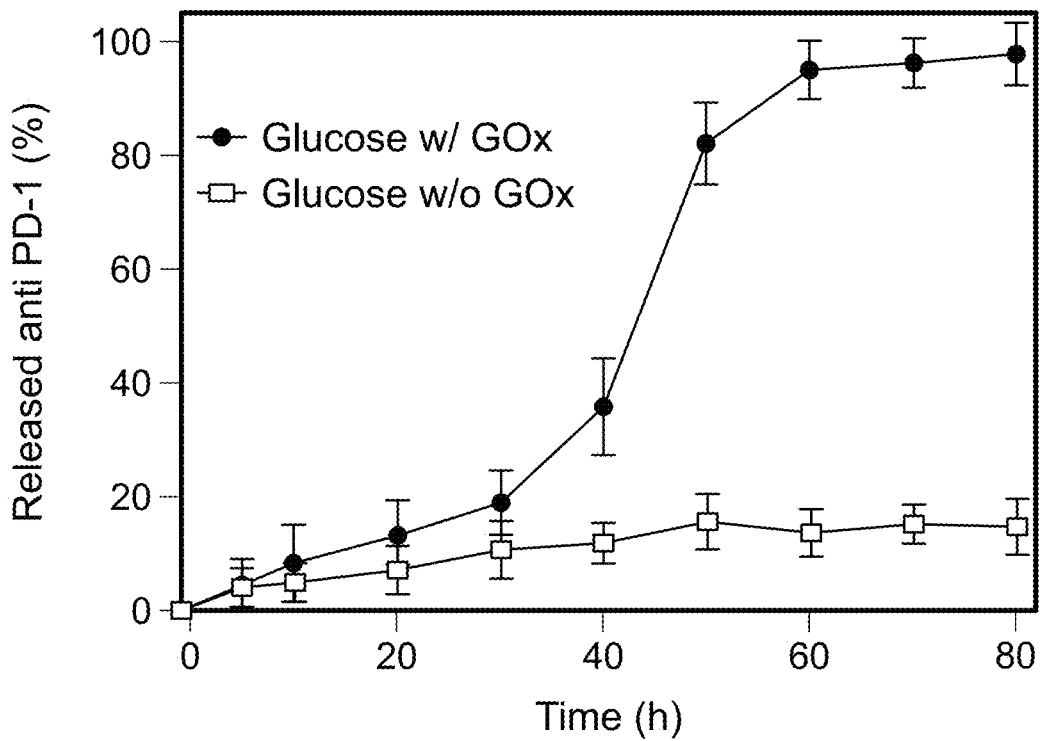
Figure 9:
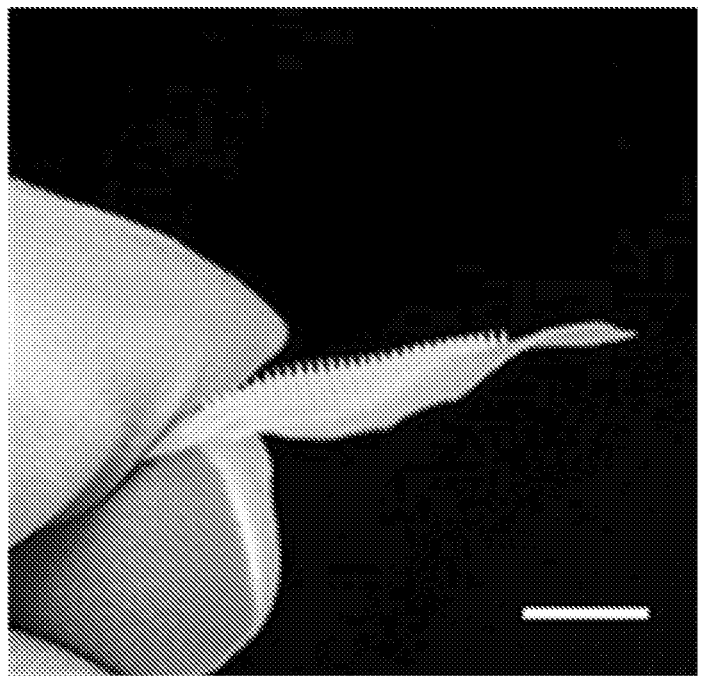
FIG. 9 shows a photograph of the microneedle (MN) patch. (Scale bar: 5 mm)
Figure 10:
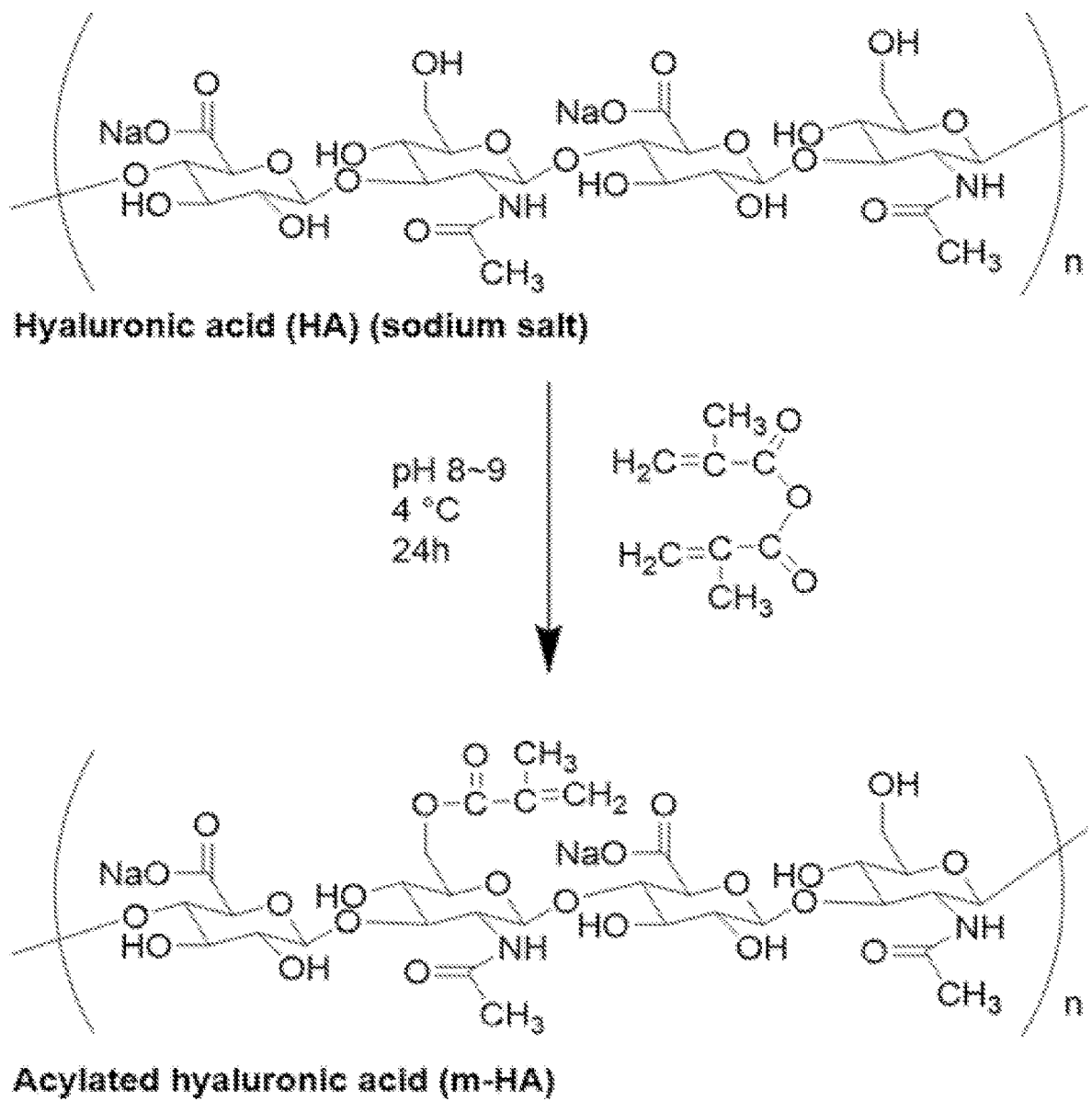
FIG. 10 shows the synthesis step of m-HA.
Figure 11:
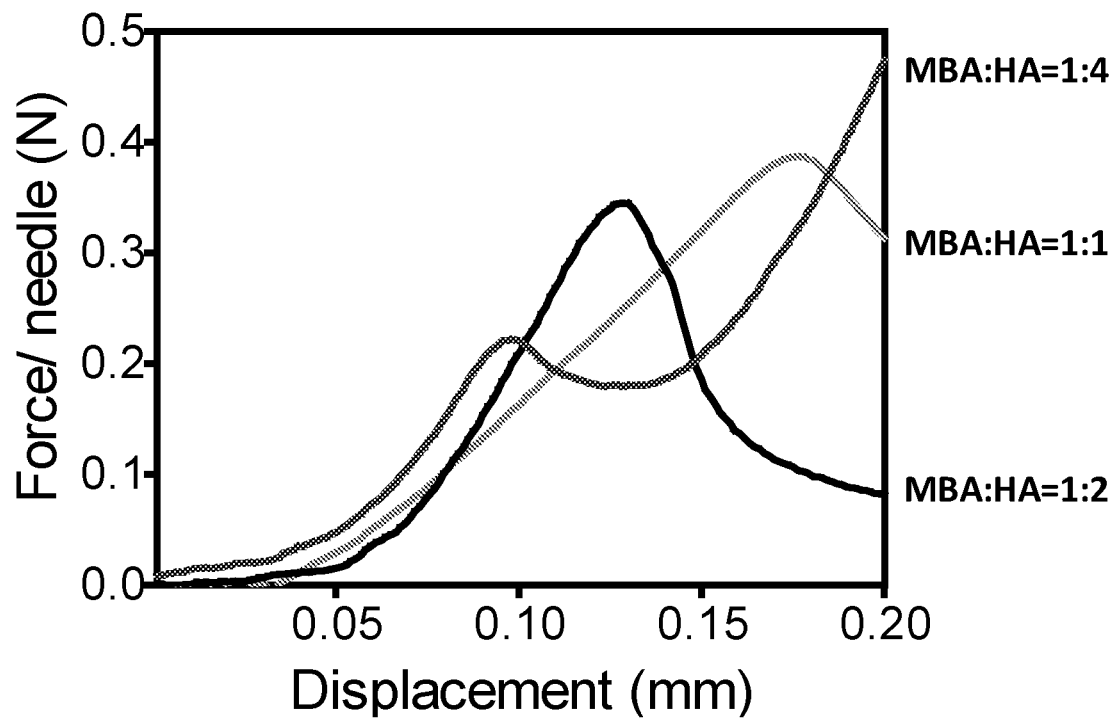
FIG. 11 shows the mechanical property of microneedles (MN) with different weight ratio between MBA and HA.
Figure 12A:
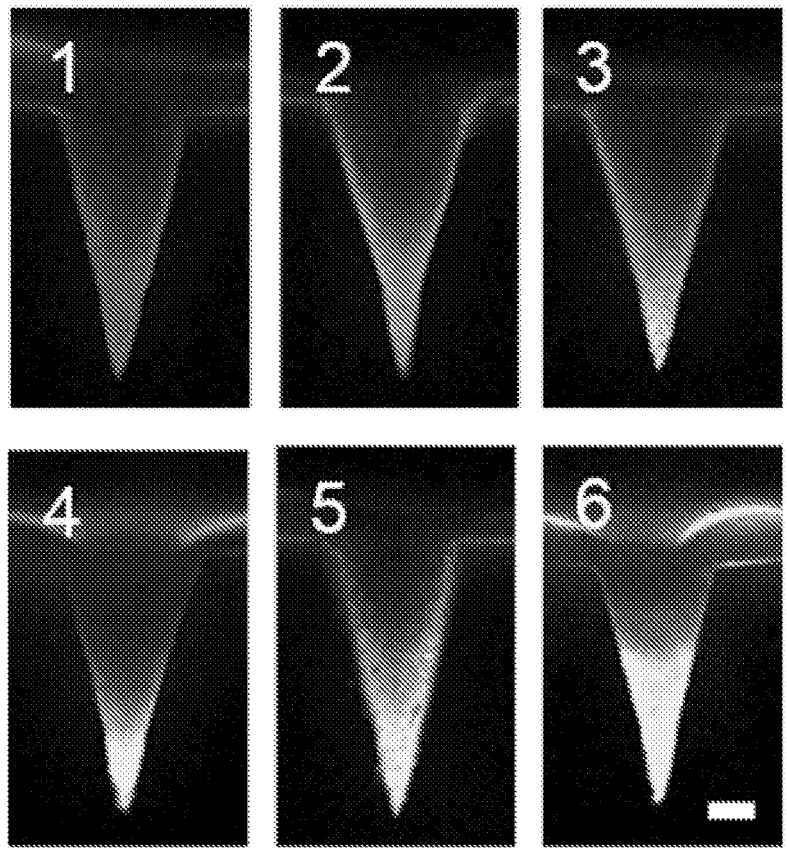
FIGS. 12A-12B show rhodamine-HA and FITC-NPs incorporation into microneedles. (a) Representative confocal images of rhodamine-labeled HA microneedles loaded with FITC-antibody loaded NPs; scale bar 100 μm. (b) Quantification of rhodamine-HA and FITC-NPs incorporation into microneedles. Analysis was performed using ImageJ measurement of total fluorescence intensity in confocal z-stacks collected along the length of microneedles, normalized to the total intensity obtained by 5 deposition times during fabrication process (results shown are averaged from n=15 individual microneedles per condition).
Figure 12B:
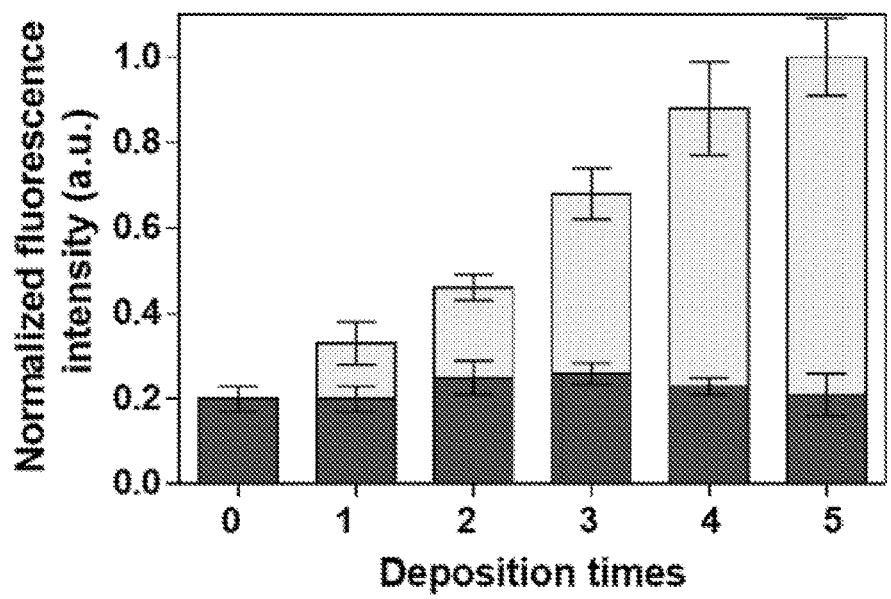
Figure 13A:
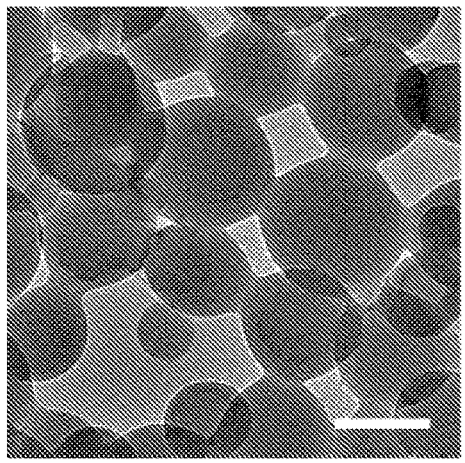
FIGS. 13A-13B show TEM images of nanoparticle (NP) morphology change before (a) and after (b) incubation in 100 mg/dL glucose solution for three days. (Scale bar: 200 μm)
Figure 13B:
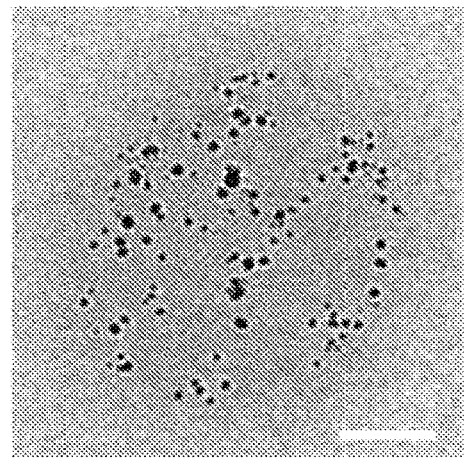
Figure 14:
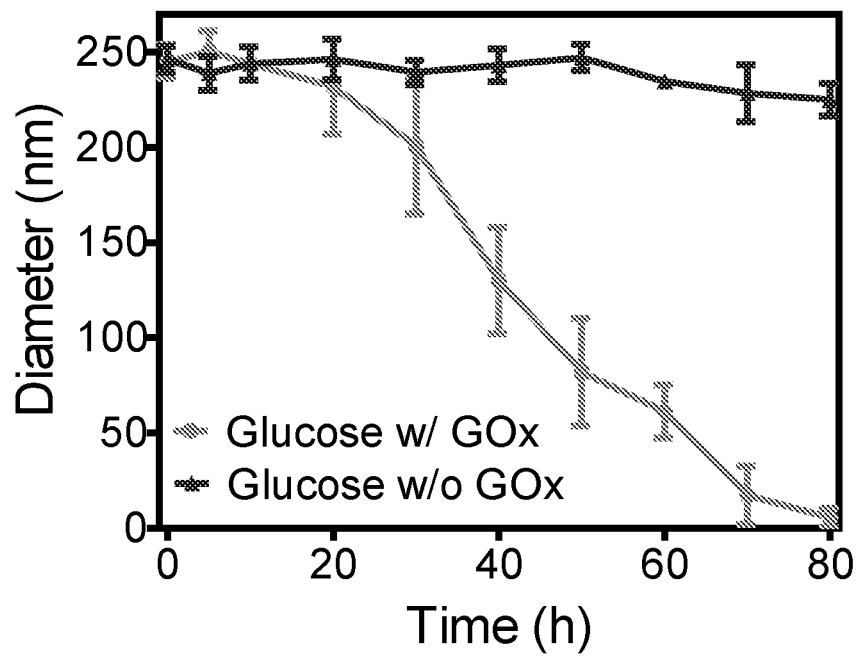
FIG. 14 shows the average hydrodynamic particle sizes change of the nanoparticles (NPs) during the incubation in 100 mg/dL glucose solution at 37° C. overtime determined by dynamic light scattering.
Figure 15:
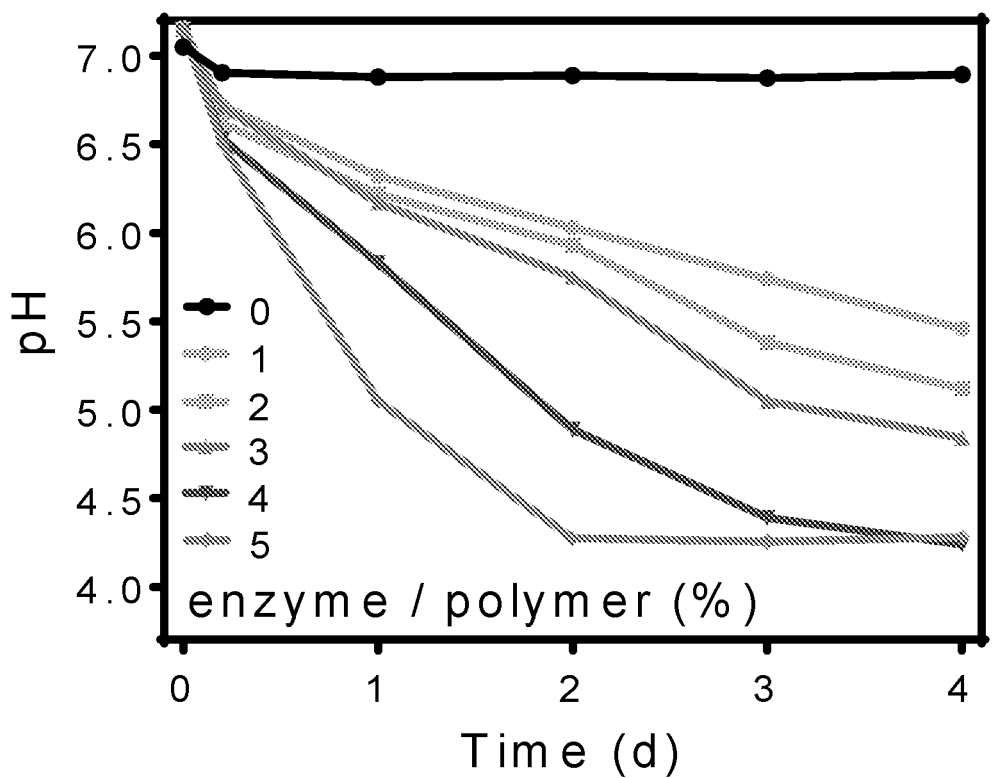
FIG. 15 shows the relevant pH changes of MNs incubated in 100 mg/dL glucose solution at 37° C. over time. Variation indicates different enzyme contents of NP during the preparation. Equilibrium was reached after the swelling of MNs in the first 10 minutes when incubated in the solution.
Figure 16:
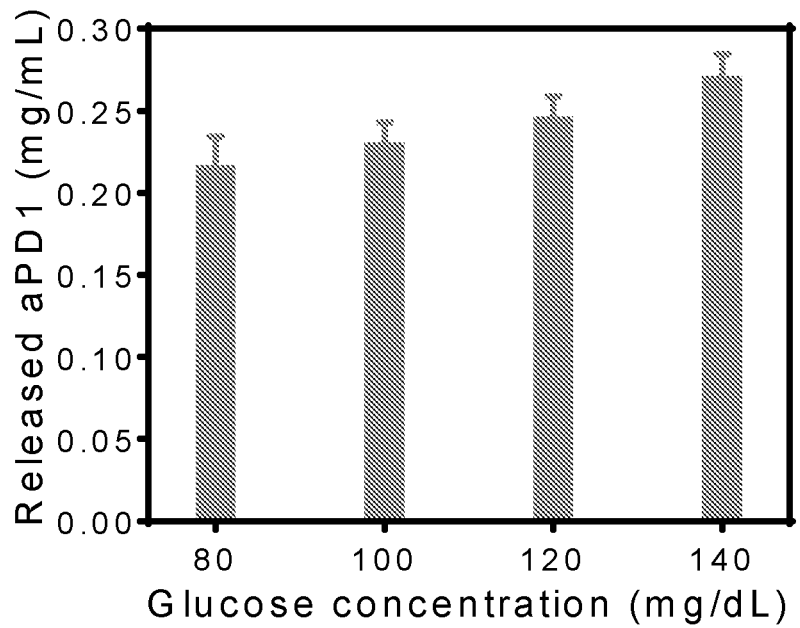
FIG. 16 shows released aPD1 from the MNs incubated in glucose solution at 37° C. for 3 days.
Figure 17:
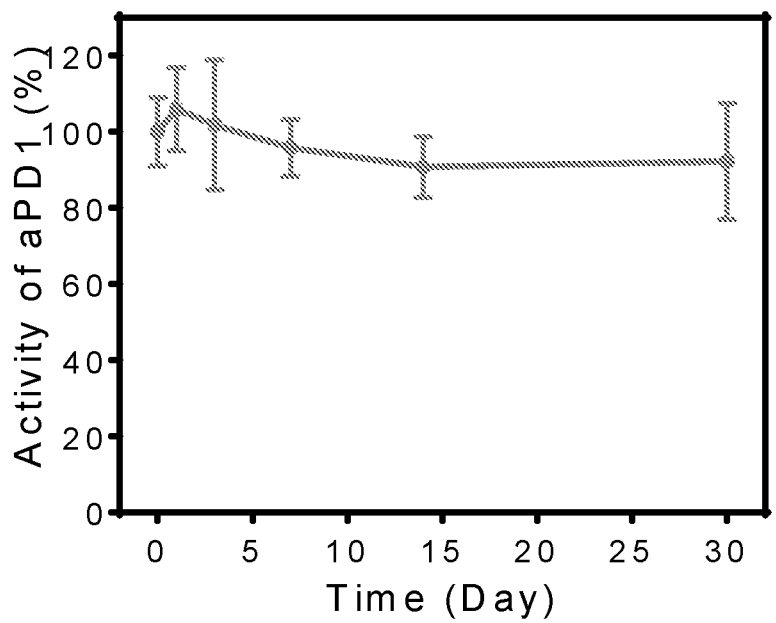
FIG. 17 shows the bioactivity of aPD1 after encapsulation in the microneedles (MNs).

The nanoparticles (NPs) were further embedded in the polymer-based MN for delivery of the encapsulated aPD1 toward the melanoma site with ease of administration. An array of 225 MNs was assembled on a 9×9 mm² patch with center-to-center interval of 600 μm (FIG. 9). Each needle was of a conical shape, with 300 μm in diameter at the base, 600 μm in height and a sharp tip tapering to a 5 μm radius of curvature (FIG. 2C). HA was selected as the structural materials for the polymeric MN due to its excellent biocompatibility, mechanical property, and tailored crosslinking density (FIG. 2F). The MN matrixes were made from crosslinked hyaluronic acid (HA), N,N'-methylenebisacrylamide (MBA), and photo initiator (Irgacure 2959, 0.05 wt %) through in situ polymerization upon exposure to UV light (365 nm at intensity of 9 mW/cm² for 30 s, a well optimized protocol with no significant photo-toxicity) (Yu, J. et al. *Proc. Natl. Acad. Sci. U.S.A.* 2015, 112, (27), 8260-8265; Bryant, S. J. et al. *J. Biomater. Sci. Polym. Ed.* 2000, 11, (5), 439-57) (FIG. 10), which provides mild reaction conditions to avoid denaturing antibodies or affecting their stability (Ye, Y. et al. *Macromol. Chem. Phys.* 2015, DOI: 10.1002/macp.201500296; DeMuth, P. C. et al. *Nat. Mater.* 2013, 12, (4), 367-376). In addition, a higher weight ratio between MBA and HA reflected enhanced mechanical property of MN (FIG. 11). Through multiple deposition, the NPs were concentrated at the tip of the needle. A regular linear increase in fluorescence intensity of the loaded drug was observed, with deposition cycles increasing up to 5 times measured by confocal microscopy (FIG. 12). The distribution of loaded NPs was further confirmed in the SEM image (FIG. 2D). A fluorescence view of a representative MN patch that contained FITC-antibody loaded NPs clearly demonstrated that the NPs were predominantly distributed at the tips of the MNs (FIG. 2E). The failure force for desired MN was quantitatively measured as 0.38 N/needle (FIG. 2F), which provided sufficient strength to facilitate skin insertion without breaking (Gittard, S. D. et al. *J. Adhes. Sci. Technol.* 2013, 27, (3), 227-243). To examine the controlled release profile of aPD1, NPs in the absence or presence of GOx were both incubated in the PBS buffer containing glucose at a normoglycemic level (100 mg/dL) in the human body. The NPs with GOx gradually dissociated in the following three days (FIG. 3A), according to the reduction of the UV absorbance at 400 nm, as well as the transparency of the incubation solution (FIG. 3D) (Tao, P. et al. *ACS Appl. Mater. Interfaces* 2011, 3, (9), 3638-3645). The SEM and TEM images further validated the conformation changes of NPs (FIGS. 3B, 13). The recorded pH values of MNs with embedded NPs dropped from 7.10 to 4.28 over time, confirming the enzymatic conversion of glucose to gluconic acid (FIG. 3C). Meanwhile, the hydrodynamic size change of the NPs with GOx steadily decreased (FIG. 14). In contrast, no noticeable dissociation was observed in the control samples without GOx. The release kinetics of aPD1 were also assessed. The tips of the needles containing NPs were incubated in glucose solution for 80 hours. A sustained release profile was achieved from the MN with GOx, whereas insignificant release was collected from the samples without GOx (FIG. 3E). In addition, the release kinetics of aPD1 could also be tailored by changing the loading amount of enzymes in the NPs (FIG. 15). Therefore the therapy efficiency of aPD1 could be further optimized by changing the enzyme's level according to different stages of melanoma. The drug release in normal glucose concentration was examined, and no significant difference was observed between different glucose levels within the normoglycemia range (FIG. 16). Collectively, these results verified that the release of aPD1 from the MNs was in a glucose-mediated and pH-dependent manner. The bioactivity of aPD1 after encapsulation in the MNs was also tested (FIG. 17). It was estimated that over 90% of aPD1 remained the bioactivity to bind the PD1 antigen after one-month storage under 4° C.

Figure 4A:
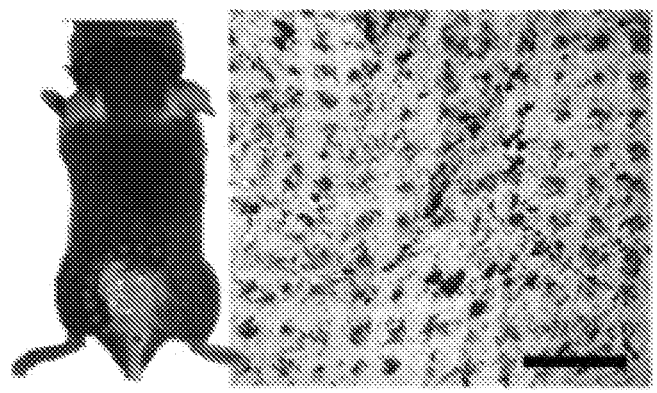
FIGS. 4A-4G show in vivo anti skin cancer treatment of aPD1 delivered by microneedles (MNs). (a) Mouse dorsum and relevant skin (the area within the red dashed line) was transcutaneously treated with a MN patch (left), with the image of the trypan blue staining showing the penetration of MN patch into the mouse skin (right). (Scale bar: 1 mm) (b) H&E-stained section of cross-sectional mouse skin area penetrated by one MN. (Scale bar: 200 μm) (c) Merged fluorescence and bright field image of the mouse skin penetrated by FITC-antibody loaded MNs. (green: aPD1) (Scale bar: 200 μm) (d) In vivo bioluminescence imaging of the B16F10 tumors of different groups indicated (1, Untreated; 2, MN-GOx; 3, Free aPD1; 4, MN-aPD1; 5, MN-GOx-aPD1). The error bars are based on the standard deviation (SD) of three mice. (e) Quantified tumor signals according to d. (f) Kaplan Meier survival curves for the treated and the control mice. Shown are eight mice per treatment group. (g) Immunofluorescence staining of tumors treated with MN-GOx-aPD1 or free aPD1 at different time points (green: aPD1, blue: nucleus) (Scale bar: 100 μm). Statistical significance was calculated by 2-way ANOVA using the Tukey post-test. Comparisons of survival curves were made using the log-rank test. P value: *, P<0.05.
Figure 4B:
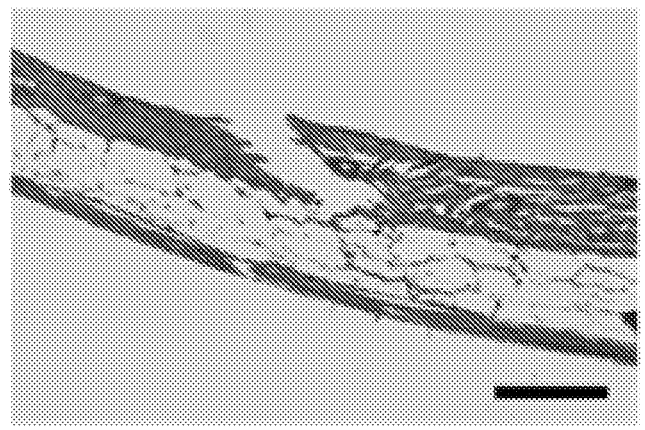
Figure 4C:
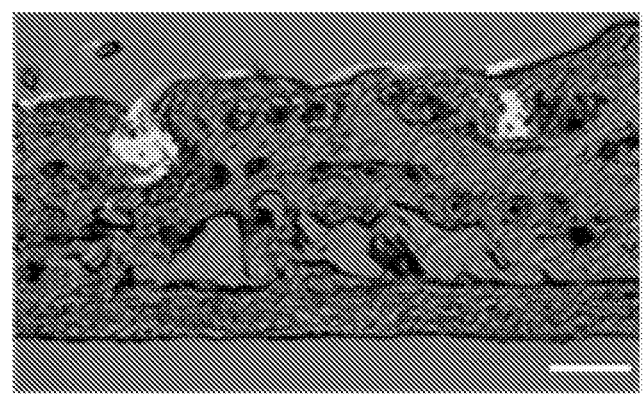
Figure 18:
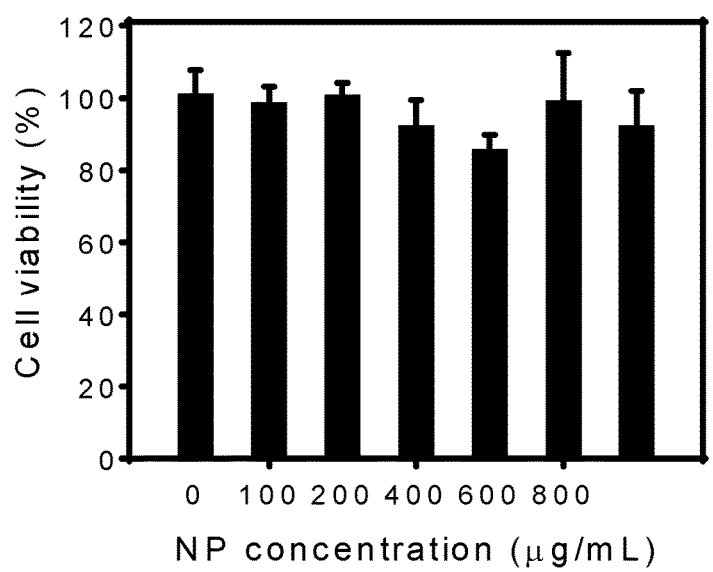
FIG. 18 shows a cytotoxicity study of empty nanoparticles (NPs) after 24 h of incubation with B16F10 cells. Error bars indicate SD (n=6).
Figure 19:
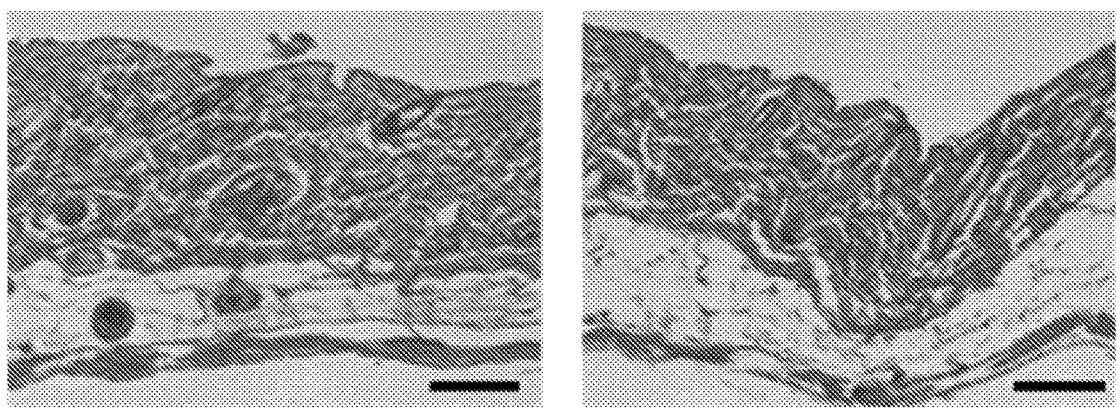
FIG. 19 shows H&E-stained skin sections administered a MN patch (left) and surrounding tissues (right) 2 d post administration. (Scale bar: 200 μm)
Figure 20:
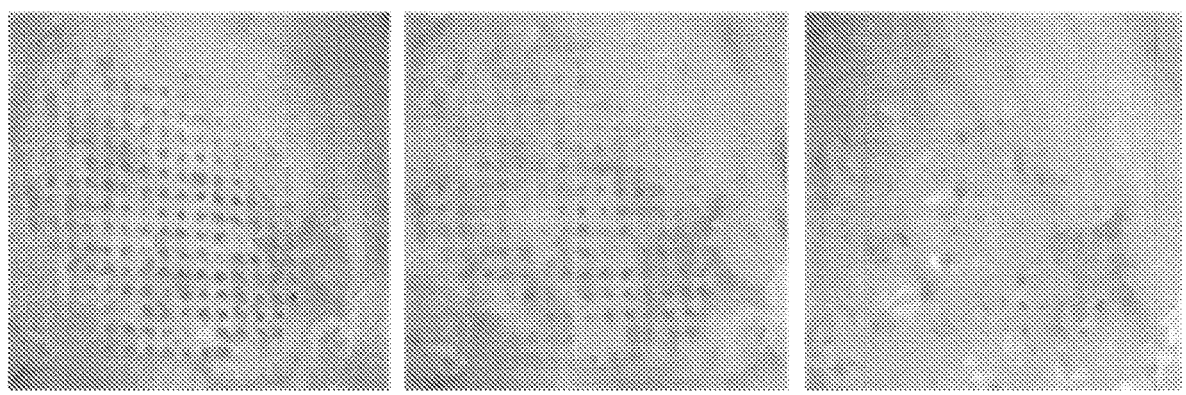
FIG. 20 shows skin puncture marks at 5 min, 10 min, and 30 min.

The obtained MN patch could penetrate the mouse skin effectively, as evidenced by the trypan blue staining and haematoxylin and eosin stain (H&E) staining (FIG. 4A-4B). Upon insertion into mouse skin, MNs penetrated to a depth of approximately 200 μm (FIG. 4B). To assess the biocompatibility of the system, the cytotoxicity of nanoparticles (NPs) and their degradation products toward B16F10 cells were evaluated at various concentrations ranging from 0.1 to 1.0 mg/mL. For all concentrations studied, m-dextran-based NPs and relevant degradation products did not show significant decrease of cell viability (FIG. 18). To further investigate the in vivo biocompatibility of the patch, it was found the skin recovered quickly after MN injection and there was no significant inflammation observed in the region 2d post-administration compared to the surrounding tissue (FIG. 19-20).

Figure 4D:
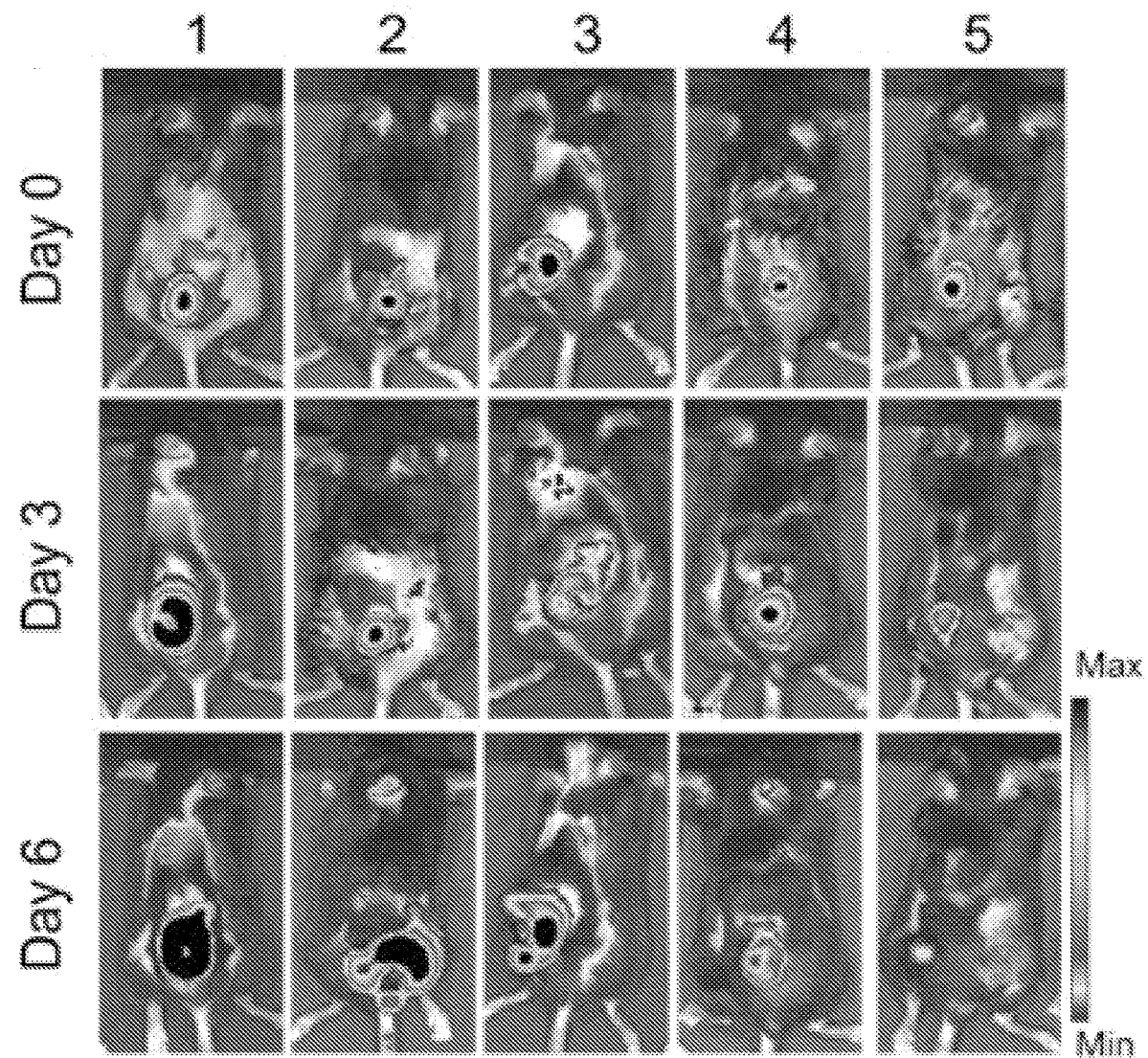
Figure 4E:
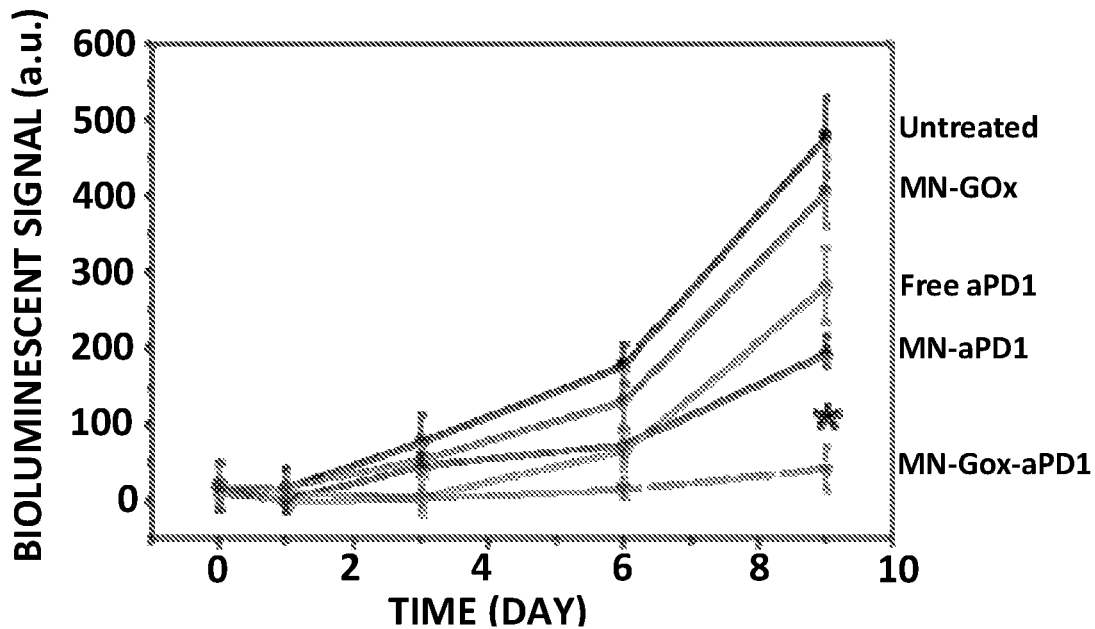
Figure 4F:
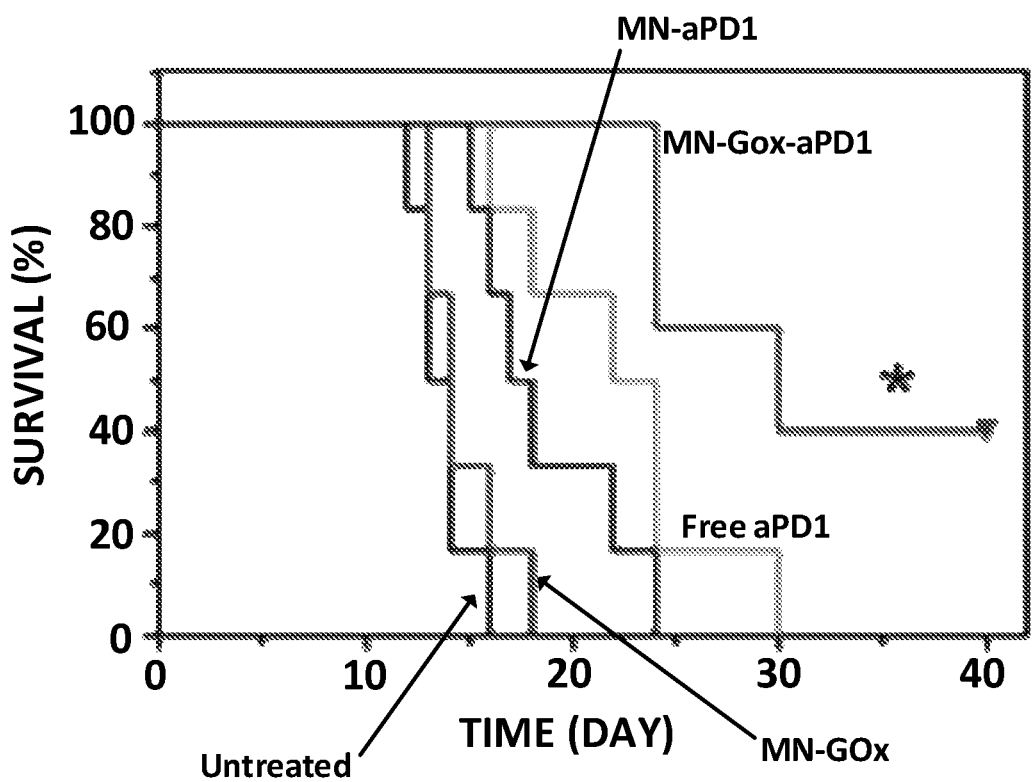
Figure 4G:
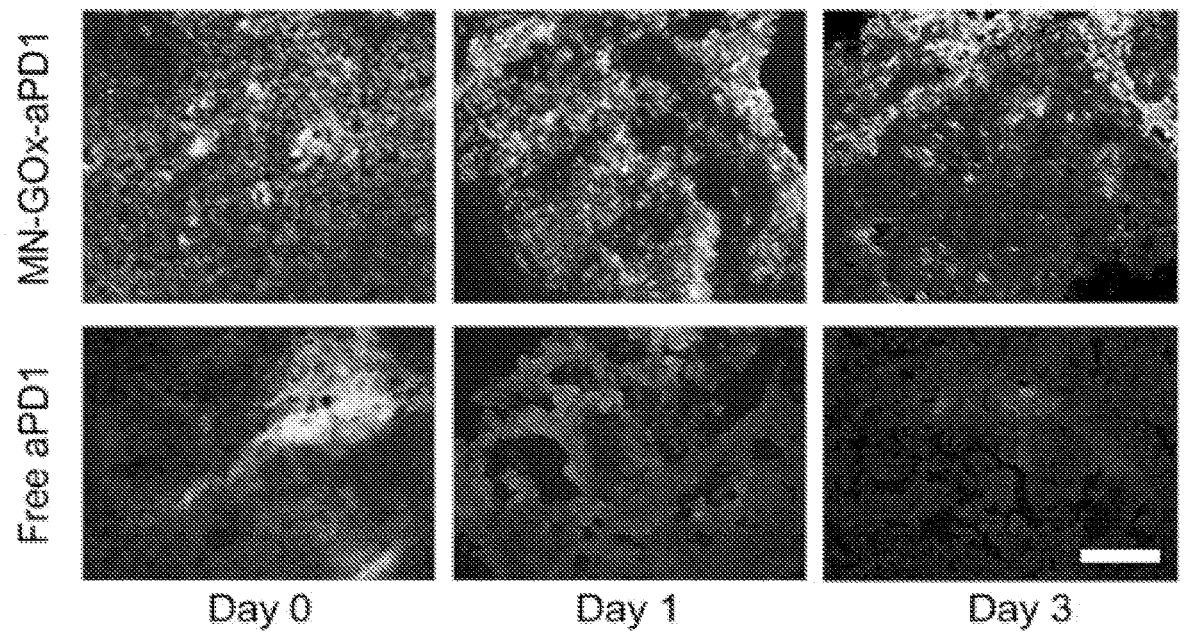

To evaluate anti-skin cancer efficiency of aPD1 delivered by MN patch, the B16F10 mouse model of melanoma was used to mimic clinical metastatic melanoma. B16F10-luc cancer cells were subcutaneously implanted in the rear dorsal area of female C57BL/6 mice. After the tumor sizes reached about 50-60 mm$^3$, MN patch (with GOx), free aPD1, and MN patch loaded with aPD1 with or w/o GOx were administered by a single local administration onto the tumor site (the area of patch was larger than tumor site). To compare the anti-melanoma efficiency between the groups, mice were treated with a relatively lower dose of aPD1 (one dosage: 1 mg/kg). In the following two weeks, the tumor growth was easily visualized and measured by the bioluminescence signals of B16F10-luc cells (FIG. 4D-4E). It was observed that the control MN patch (with GOx) treatment had little effect on the tumor regression compared to the untreated group. While mice treated with free aPD1 showed a delayed tumor growth in the first several days, tumor relapse dramatically occurred afterwards. The effect on the tumor regression in groups treated with MN-anti-PD-1 without GOx loading was limited due to the restricted release of aPD1. In contrast, mice receiving aPD1 delivered by MN patch (with GOx) showed a significant sustained tumor inhibition, some of tumors even disappeared after treatment. Importantly, it was found that 40% of mice still survived 40 days after treated with aPD1-GOx-MN patch. In sharp contrast, none of the mice survived in the control groups (FIG. 4F). This remarkable anti-tumor efficacy may be attributed to the sustained release of aPD1 by MNs in the tumor site and the enhanced retention of aPD1 in a tumor microenvironment.

Next, the treated tumors were collected for the immunostaining at different time points. As a control, when free aPD1 was directly intratumorally injected, strong antibody signals were found in the tumor site at administration date (day 0). However, the signals diminished significantly in the following three days, indicating the diffusion of antibodies into other tissues, whereas aPD1 delivered by MN can lead to continuously observed signals of antibodies found in the tumor site. The existence of aPD1 in the tumor microenvironment plays a key role in altering the balance of suppressive versus cytotoxic responses in the microenvironment of tumor (Zou, W. Nat. Rev. Cancer 2005, 5, (4), 263-274), resulting in immune cells recognizing and destroying cancer cells.

Figure 5A:
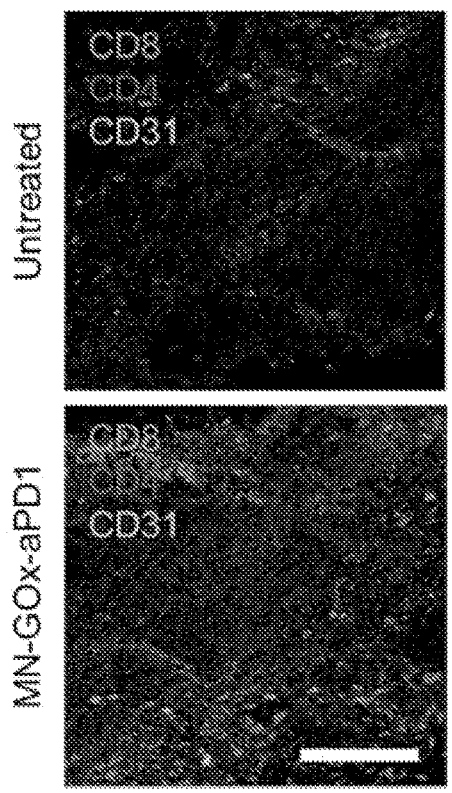
FIGS. 5A-5C show the characterization of T cell infiltration into tumors after treatment of aPD1 delivered by microneedles (MNs). (a) Immunofluorescence of tumours showed CD4+ T cells and CD8+ T cells infiltration (Scale bar: 100 μm). (b) Representative plots of T cells in treated tumors analyzed by flow cytometry. (Gated on CD3+ T cells). (c) Proportion of tumor-infiltrating CD8+ T cells according to b. The error bars are based on the SD of three mice. Statistical significance was calculated by 2-way ANOVA using the Tukey post-test. P value: *, P<0.05.
Figure 5B:
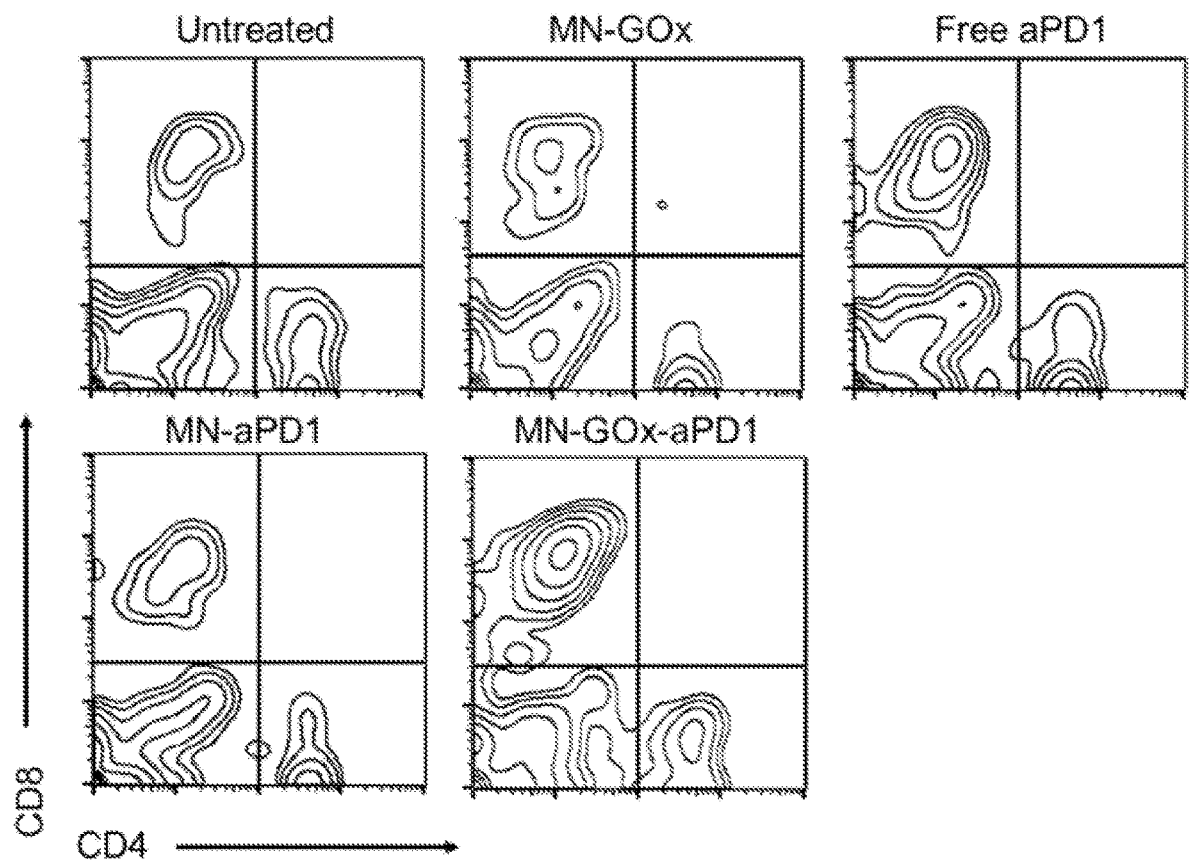
Figure 5C:
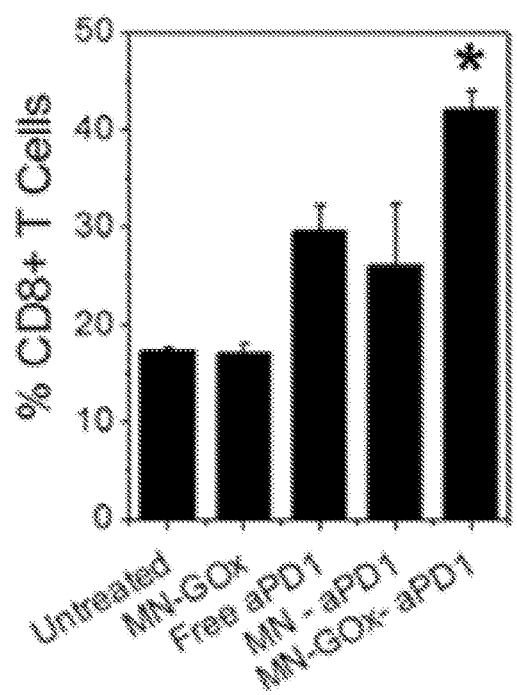

To study the infiltration of immune cells into the tumor site after treatment, the tumor-infiltrating lymphocytes (TILs) from the tumor were then harvested and analyzed by the immunofluorescence and flow cytometry 10 days after treatment. Immunofluorescence staining revealed that the untreated tumors had limited T-cell infiltration (FIG. 5A). In contrast, tumors from MN-GOx-aPD1 treated mice were remarkably infiltrated by both CD8+ and CD4+ T cells. The percentage of CD8+ T cells in the tumor after the aPD1 delivered by MN patch was 1.5-fold of that in the free aPD1 treatment group, and two-fold compared to that in the control MNs or untreated groups (FIG. 5B-5C).

Figure 21A:
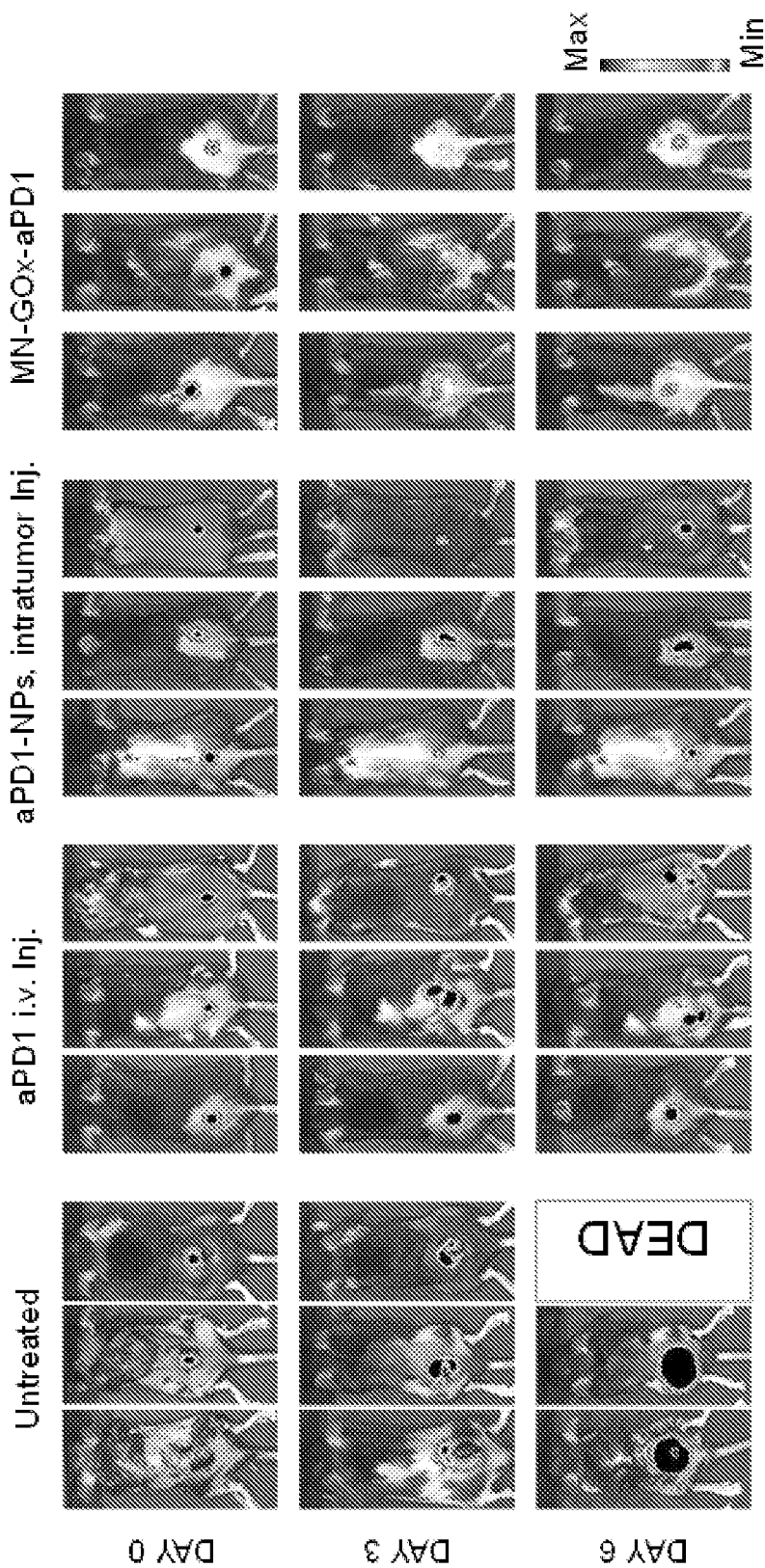
FIGS. 21A-21C show the effects of aPD1 on B16F10 tumors. (a) In vivo bioluminescence imaging of the B16F10 tumors of different groups indicated (1, Untreated; 2, aPD1 i.v. injection; 3, intratumoral injection of the NPs loaded with aPD1; 4, MN-GOx-aPD1). The error bars are based on the standard deviation (SD) (n=3). (b) Quantified tumor signals according to a. (c) Kaplan Meier survival curves for the treated and the control groups (n=7 or 8). (P value: *, P<0.05)
Figure 21B:
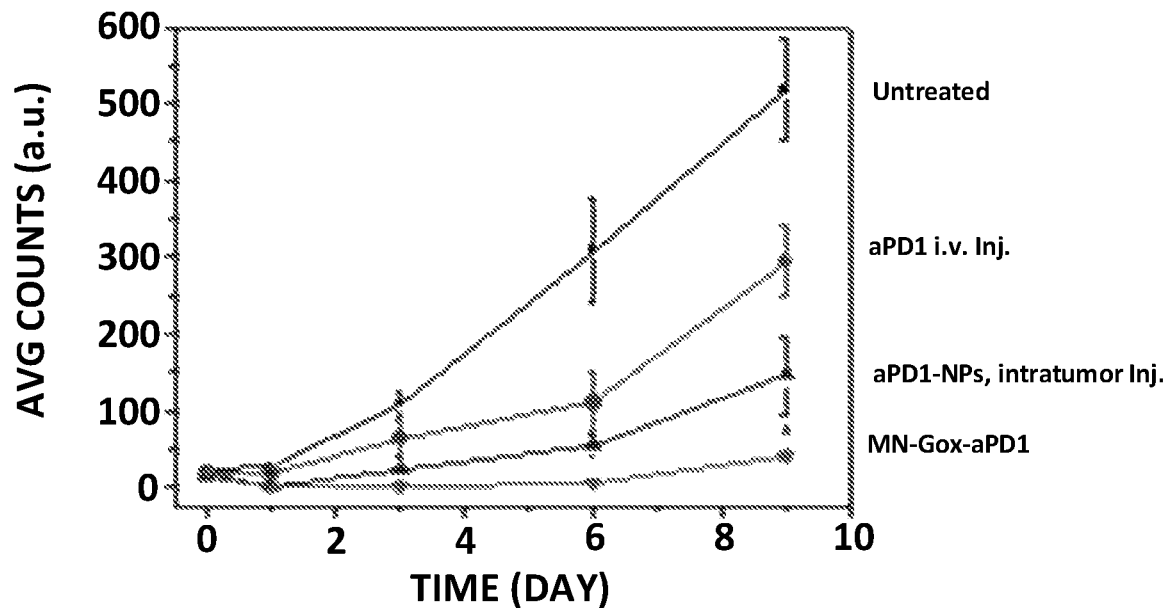
Figure 21C:
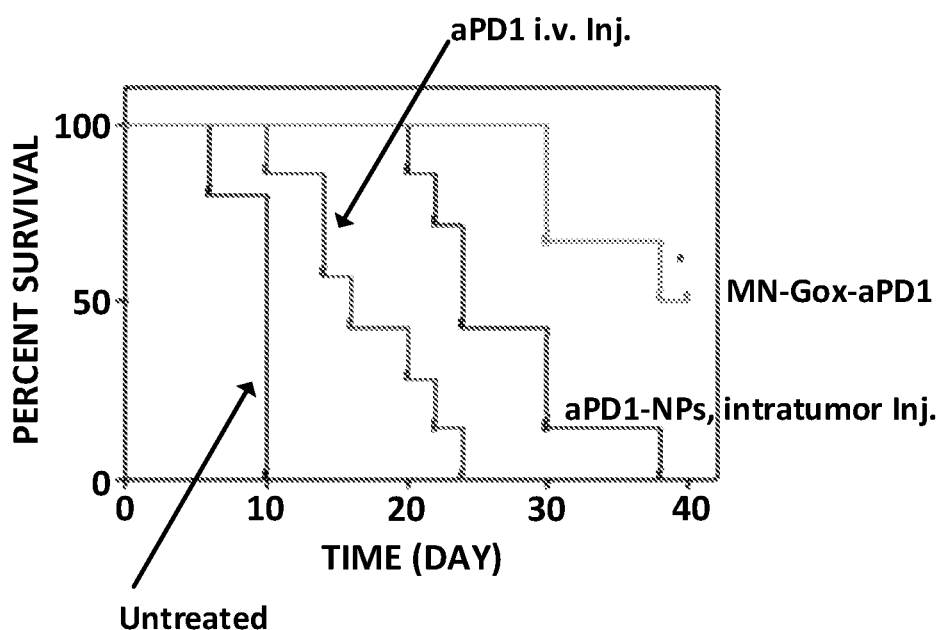

In a further step, the anti-melanoma efficacy of the MN patch was compared to the previous method including systemic administration of aPD1 by intravenous (i.v.) injection or directly intratumoral injection of the self-dissociated NPs loaded with aPD1 (1 mg/kg). As shown in FIG. 21, mice treated with MN-GOx-aPD1 showed the significant anti-tumor efficiency compared with other treatments. About 50% of mice survived with undetectable tumor after being treated with aPD1-GOx-MN patch within 40 days. Systemic administration of aPD1 or intratumoral injection of the self-dissociated aPD1-NPs modestly increased average survival times but none of mice survived in 40 days. These results clearly indicated that our MN enhanced retention of aPD1 in the tumor following administration, resulting in an enhanced cancer immunotherapy by aPD1 checkpoint inhibition.

Figure 22A:
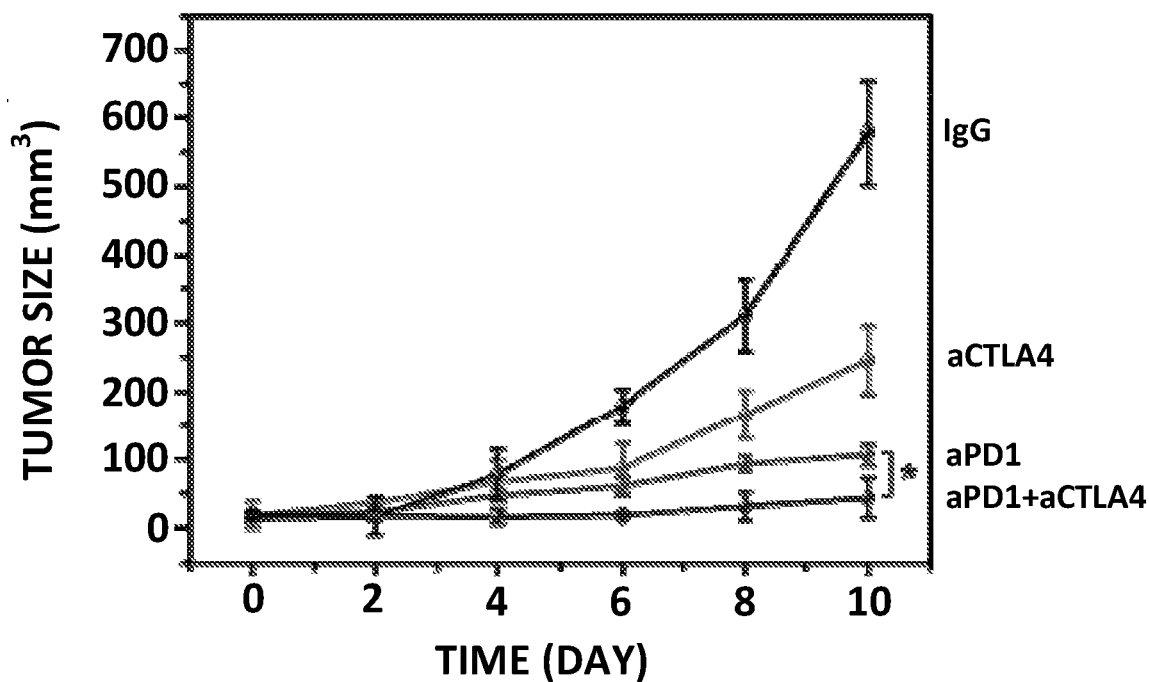
FIGS. 22A-22B show the effects of aPD1 and aCTLA4 treatment on growth of tumors. (a) Tumor growth curves of different groups of mice after various treatments indicated (7-8 mice per group). Error bars are based on SEM. (b) The survival curves of mice at 60 days after various treatments indicated. Statistical significance was calculated by 2-way ANOVA using the Tukey post-test. (P value: *, P<0.05).
Figure 22B:
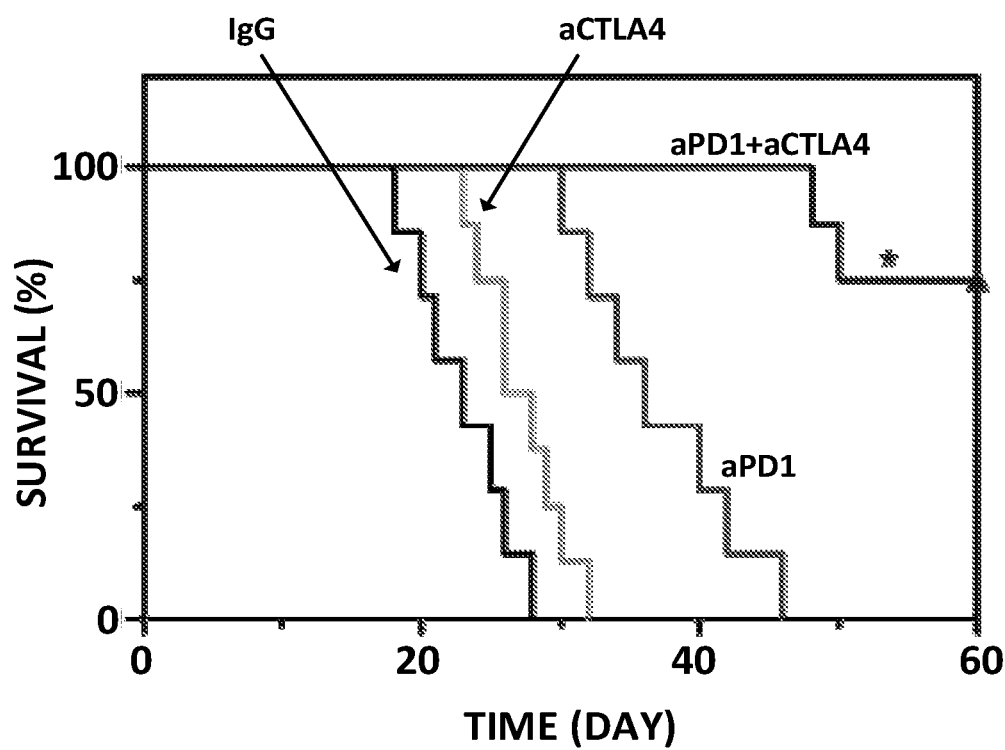

Anti-CTLA4 is another checkpoint antibody that promotes T-cell activation and disables T regulatory cells (Tregs) (Pardoll, D. M. Nat. Rev. Cancer 2012, 12, (4), 252-264; Wang, C. et al. Adv. Mater. 2014, 26, (48), 8154-8162). Due to the increased CTLA4 expression observed on TILs after aPD1 treatment (Lussier, D. M. et al. J. Immunother. Cancer 2015, 3, (1), 1-11; Curran, M. A. et al. Proc. Natl. Acad. Sci. U.S.A 2010, 107, (9), 4275-4280), the combination of anti-CTLA4 antibody (aCTLA4) and aPD1 co-delivery by MNs was examined for an increase in the efficacy of these therapies with half dose of antibodies. Mice carrying B16F10 melanoma were treated with MN-GOx patch loaded with IgG (1 mg/kg, isotype control), aCTLA4 (1 mg/kg), aPD1 (1 mg/kg), or co-loaded with aCTLA4 and aPD1 (0.5 mg/kg, respectively). As shown in FIG. 22A, a remarkable synergistic effect was achieved by combination of aCTLA4 and aPD1 co-delivered via MNs in comparison to aCTLA4 alone, aPD1 alone, or IgG MNs treated mice. Moreover, combination of aCTLA4 and aPD1 delivered by MNs resulted in complete control of melanoma with long-term disease-free survival in roughly 70% of mice treated with a combination of aCTLA4 and aPD1 in 60 days (FIG. 22B).

In summary, the MN patch-assisted immunotherapy can deliver aPD1 for the enhanced treatment of the skin cancer. The patch can painlessly penetrate the epidermis and become submerged in the interstitial fluid to efficiently deliver its payload to the tumor microenvironment. The nanoparticles (NPs) in each needle contain aPD1 and the glucose oxidase enzyme, which promotes the "self-dissociation" of NPs and subsequently facilitates the release of aPD1 in a sustained manner. In vivo studies using mouse models with melanoma showed that a single administration of the MN patch inhibited tumor growth superior to those obtained with intratumor (i.t.) injection of the same dose. Moreover, the MN co-loaded with aCTLA-4 and aPD1 resulted in synergistic treatment of melanoma. Taken together, these results show that the MN-assisted delivery system provides a new platform technology for administration of cancer immunotherapeutics with improved safety, immunogenicity and logistical operations.

REFERENCES

The disclosures of all articles and references, including patent applications and publications, are incorporated by reference for all purposes.

1. Simões, M.; Sousa, J.; Pais, A. *Cancer Lett.* 2015, 357, (1), 8-42.
2. Rogers, H. W.; Weinstock, M. A.; Harris, A. R.; Hinckley, M. R.; Feldman, S. R.; Fleischer, A. B.; Coldiron, B. M. *Arch. Dermatol.* 2010, 146, (3), 283-287.
3. Chinembiri, T. N.; du Plessis, L. H.; Gerber, M.; Hamman, J. H.; du Plessis, *J. Molecules* 2014, 19, (8), 11679-11721.
4. Pardoll, D. M. *Nat. Rev. Cancer* 2012, 12, (4), 252-264.
5. Gubin, M. M.; Zhang, X.; Schuster, H.; Caron, E.; Ward, J. P.; Noguchi, T.; Ivanova, Y.; Hundal, J.; Arthur, C. D.; Krebber, W.-J.; Mulder, G. E.; Toebes, M.; Vesely, M. D.; Lam, S. S. K.; Korman, A. J.; Allison, J. P.; Freeman, G. J.; Sharpe, A. H.; Pearce, E. L.; Schumacher, T. N.; Aebersold, R.; Rammensee, H.-G.; Melief, C. J. M.; Mardis, E. R.; Gillanders, W. E.; Artyomov, M. N.; Schreiber, R. D. *Nature* 2014, 515, (7528), 577-581.
6. Tumeh, P. C.; Harview, C. L.; Yearley, J. H.; Shintaku, I. P.; Taylor, E. J. M.; Robert, L.; Chmielowski, B.; Spasic, M.; Henry, G.; Ciobanu, V.; West, A. N.; Carmona, M.; Kivork, C.; Seja, E.; Cherry, G.; Gutierrez, A. J.; Grogan, T. R.; Mateus, C.; Tomasic, G.; Glaspy, J. A.; Emerson, R. O.; Robins, H.; Pierce, R. H.; Elashoff, D. A.; Robert, C.; Ribas, A. *Nature* 2014, 515, (7528), 568-571.
7. Chinai, J. M.; Janakiram, M.; Chen, F.; Chen, W.; Kaplan, M.; Zang, X. *Trends Pharmacol. Sci.* 2015, 36, (9), 587-595.
8. Gubin, M. M.; Zhang, X.; Schuster, H.; Caron, E.; Ward, J. P.; Noguchi, T.; Ivanova, Y.; Hundal, J.; Arthur, C. D.; Krebber, W.-J. *Nature* 2014, 515, (7528), 577-581.
9. Kyi, C.; Postow, M. A. *FEBS Letters* 2014, 588, (2), 368-376.
10. Sullivan, R. J.; Flaherty, K. T. *Nat. Rev. Clin. Oncol.* 2015, 12, (11), 625-626.
11. Topalian, S. L.; Hodi, F. S.; Brahmer, J. R.; Gettinger, S. N.; Smith, D. C.; McDermott, D. F.; Powderly, J. D.; Carvajal, R. D.; Sosman, J. A.; Atkins, M. B.; Leming, P. D.; Spigel, D. R.; Antonia, S. J.; Horn, L.; Drake, C. G.; Pardoll, D. M.; Chen, L.; Sharfman, W. H.; Anders, R. A.; Taube, J. M.; McMiller, T. L.; Xu, H.; Korman, A. J.; Jure-Kunkel, M.; Agrawal, S.; McDonald, D.; Kollia, G. D.; Gupta, A.; Wigginton, J. M.; Sznol, M. *N. Engl. J. Med.* 2012, 366, (26), 2443-2454.
12. Topalian, S. L.; Sznol, M.; McDermott, D. F.; Kluger, H. M.; Carvajal, R. D.; Sharfman, W. H.; Brahmer, J. R.; Lawrence, D. P.; Atkins, M. B.; Powderly, J. D. *J. Clin. Oncol.* 2014, 32, (10), 1020-1030.
13. Larkin, J.; Chiarion-Sileni, V.; Gonzalez, R.; Grob, J. J.; Cowey, C. L.; Lao, C. D.; Schadendorf, D.; Dummer, R.; Smylie, M.; Rutkowski, P.; Ferrucci, P. F.; Hill, A.; Wagstaff, J.; Carlino, M. S.; Haanen, J. B.; Maio, M.; Marquez-Rodas, I.; McArthur, G. A.; Ascierto, P. A.; Long, G. V.; Callahan, M. K.; Postow, M. A.; Grossmann, K.; Sznol, M.; Dreno, B.; Bastholt, L.; Yang, A.; Rollin, L. M.; Horak, C.; Hodi, F. S.; Wolchok, J. D. *N. Engl. J. Med.* 2015, 373, (1), 23-34.
14. Sharma, P.; Allison, J. P. *Cell* 2015, 161, (2), 205-14.
15. Topalian, S. L.; Hodi, F. S.; Brahmer, J. R.; Gettinger, S. N.; Smith, D. C.; McDermott, D. F.; Powderly, J. D.; Carvajal, R. D.; Sosman, J. A.; Atkins, M. B. *N. Engl. J. Med.* 2012, 366, (26), 2443-2454.
16. Chapman, A. P. *Adv. Drug Deliv. Rev.* 2002, 54, (4), 531-545.
17. Mitragotri, S.; Burke, P. A.; Langer, R. *Nat. Rev. Drug Discovery* 2014, 13, (9), 655-72.
18. Tong, R.; Langer, R. *Cancer J.* 2015, 21, (4), 314-21.
19. Chen, J.; Wang, D.; Xi, J.; Au, L.; Siekkinen, A.; Warsen, A.; Li, Z.-Y.; Zhang, H.; Xia, Y.; Li, X. *Nano lett.* 2007, 7, (5), 1318-1322.
20. Timko, B. P.; Arruebo, M.; Shankarappa, S. A.; McAlvin, J. B.; Okonkwo, O. S.; Mizrahi, B.; Stefanescu, C. F.; Gomez, L.; Zhu, J.; Zhu, A. *Proc. Natl. Acad. Sci. U.S.A.* 2014, 111, (4), 1349-1354.
21. Irvine, D. J.; Hanson, M. C.; Rakhra, K.; Tokatlian, T. *Chem. Rev.* 2015, 115, (19), 11109-46.
22. Prausnitz, M. R. *Nat. Mater.* 2015, 14, (5), 470-1.
23. Chiappini, C.; De Rosa, E.; Martinez, J.; Liu, X.; Steele, J.; Stevens, M.; Tasciotti, E. *Nat. Mater.* 2015.
24. Yu, J.; Zhang, Y.; Ye, Y.; DiSanto, R.; Sun, W.; Ranson, D.; Ligler, F. S.; Buse, J. B.; Gu, Z. *Proc. Natl. Acad. Sci. U.S.A.* 2015, 112, (27), 8260-8265.
25. Sullivan, S. P.; Murthy, N.; Prausnitz, M. R. *Adv. Mater.* 2008, 20, (5), 933-938.
26. Prausnitz, M. R. *Adv. Drug Deliv. Rev.* 2004, 56, (5), 581-587.
27. Lee, D.-K.; Kim, S. V.; Limansubroto, A. N.; Yen, A.; Soundia, A.; Wang, C.-Y.; Shi, W.; Hong, C.; Tetradis, S.; Kim, Y. *ACS Nano* 2015, 9, (11), 11490-11501.
28. Harvey, A. J.; Kaestner, S. A.; Sutter, D. E.; Harvey, N. G.; Mikszta, J. A.; Pettis, R. J. *Pharm. Res.* 2010, 28, (1), 107-116.
29. Lu, Y.; Sun, W.; Gu, Z. *J. Control Release* 2014, 194, 1-19.
30. Mura, S.; Nicolas, J.; Couvreur, P. *Nat. Mater.* 2013, 12, (11), 991-1003.
31. Chen, Q.; Ke, H.; Dai, Z.; Liu, Z. *Biomaterials* 2015, 73, 214-230.
32. Naessens, M.; Cerdobbel, A.; Soetaert, W.; Vandamme, E. J. *J. Ind. Microbiol. Biotechnol.* 2005, 32, (8), 323-334.
33. Bachelder, E. M.; Beaudette, T. T.; Broaders, K. E.; Dashe, J.; Fréchet, J. M. *J. J. Am. Chem. Soc.* 2008, 130, (32), 10494-10495.
34. Gu, Z.; Aimetti, A. A.; Wang, Q.; Dang, T. T.; Zhang, Y.; Veiseh, O.; Cheng, H.; Langer, R. S.; Anderson, D. G. *ACS Nano* 2013, 7, (5), 4194-4201.
35. Bryant, S. J.; Nuttelman, C. R.; Anseth, K. S. *J. Biomater. Sci. Polym. Ed.* 2000, 11, (5), 439-57.
36. Ye, Y.; Yu, J.; Gu, Z. *Macromol. Chem. Phys.* 2015, DOI: 10.1002/macp.201500296.
37. DeMuth, P. C.; Min, Y.; Huang, B.; Kramer, J. A.; Miller, A. D.; Barouch, D. H.; Hammond, P. T.; Irvine, D. J. *Nat. Mater.* 2013, 12, (4), 367-376.
38. Gittard, S. D.; Chen, B.; Xu, H.; Ovsianikov, A.; Chichkov, B. N.; Monteiro-Riviere, N. A.; Narayan, R. J. *J. Adhes. Sci. Technol.* 2013, 27, (3), 227-243.

39. Tao, P.; Viswanath, A.; Schadler, L. S.; Benicewicz, B. C.; Siegel, R. W. *ACS Appl. Mater. Interfaces* 2011, 3, (9), 3638-3645.
40. Zou, W. *Nat. Rev. Cancer* 2005, 5, (4), 263-274.
41. Pardoll, D. M. *Nat. Rev. Cancer* 2012, 12, (4), 252-264.
42. Wang, C.; Xu, L.; Liang, C.; Xiang, J.; Peng, R.; Liu, Z. *Adv. Mater.* 2014, 26, (48), 8154-8162.
43. Lussier, D. M.; Johnson, J. L.; Hingorani, P.; Blattman, J. N. *J. Immunother. Cancer* 2015, 3, (1), 1-11.
44. Curran, M. A.; Montalvo, W.; Yagita, H.; Allison, J. P. *Proc. Natl. Acad. Sci. U.S.A* 2010, 107, (9), 4275-4280.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:

1. A method for treating a skin cancer in a subject in need thereof, comprising:
    providing a microneedle patch to a subject, wherein the microneedle patch comprises:
        a plurality of microneedles each having a base end and a tip;
        a substrate to which the base ends of the microneedles are attached or integrated;
        acid-degradable nanoparticles, wherein the nanoparticles encapsulate an immunotherapeutic agent and a pH altering agent;
    inserting the microneedles into a biological barrier, wherein the pH altering agent decreases the pH within the acid-degradable nanoparticles, and wherein the decrease in the pH degrades the nanoparticle and releases the immunotherapeutic agent into the subject in a controlled-release manner;
    wherein the immunotherapeutic agent comprises an anti-PD1 antibody and an anti-CTLA4 antibody.

2. The method of claim 1, wherein the skin cancer is melanoma.

3. The method of claim 1, wherein the pH altering agent is glucose oxidase.

4. The method of claim 1, wherein the acid-degradable nanoparticles comprise modified dextran.

5. The method of claim 1, wherein the microneedles comprise hyaluronic acid.

6. The method of claim 1, wherein the anti-PD1 antibody is nivolumab.

7. The method of claim 1, wherein the anti-PD1 antibody is pembrolizumab.

8. The method of claim 1, wherein the anti-CTLA4 antibody is ipilimumab.

9. The method of claim 1, wherein the acid-degradable nanoparticles further comprise a surfactant.

10. The method of claim 9, wherein the surfactant is alginate.

* * * * *